United States Patent
Franco et al.

(10) Patent No.: US 10,546,719 B2
(45) Date of Patent: Jan. 28, 2020

(54) FACE-ON, GAS-ASSISTED ETCHING FOR PLAN-VIEW LAMELLAE PREPARATION

(71) Applicant: FEI Company, Hillsboro, OR (US)

(72) Inventors: Noel Thomas Franco, Hillsboro, OR (US); Kenny Mani, Beaverton, OR (US); Chad Rue, Portland, OR (US); Joe Christian, Portland, OR (US); Jeffrey Blackwood, Portland, OR (US)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 15/987,847

(22) Filed: May 23, 2018

(65) Prior Publication Data

US 2018/0350558 A1 Dec. 6, 2018

Related U.S. Application Data

(60) Provisional application No. 62/514,248, filed on Jun. 2, 2017.

(51) Int. Cl.
| | |
|---|---|
| *H01J 37/305* | (2006.01) |
| *H01L 21/67* | (2006.01) |
| *H01L 21/263* | (2006.01) |
| *H01L 21/3065* | (2006.01) |
| *H01J 37/22* | (2006.01) |
| *G01N 1/44* | (2006.01) |
| *G01N 1/28* | (2006.01) |

(52) U.S. Cl.
CPC .......... *H01J 37/3053* (2013.01); *G01N 1/286* (2013.01); *G01N 1/44* (2013.01); *H01J 37/222* (2013.01); *H01L 21/2633* (2013.01); *H01L 21/67069* (2013.01); *H01J 2237/31745* (2013.01); *H01L 21/3065* (2013.01)

(58) Field of Classification Search
CPC ................ H01J 37/3053; H01J 37/222; H01J 2237/31745; G01N 1/286; G01N 1/32; G01N 1/44; G01N 2001/2873; H01L 21/2633; H01L 21/67069; H01L 21/3065; H01L 21/32136
USPC ... 250/492.1, 492.2, 492.21, 492.22, 492.23, 250/492.3
See application file for complete search history.

(56) References Cited

U.S. PATENT DOCUMENTS

| | | |
|---|---|---|
| 5,435,850 A | 7/1995 | Rasmussen |
| 5,851,413 A | 12/1998 | Casella et al. |

(Continued)

FOREIGN PATENT DOCUMENTS

| | | |
|---|---|---|
| EP | 0706199 A1 | 4/1996 |
| WO | 2015003671 A2 | 1/2015 |

*Primary Examiner* — Nicole M Ippolito

(57) ABSTRACT

Method for preparing site-specific, plan-view lamellae from multilayered microelectronic devices. A focused ion beam that is directed, with an etch-assisting gas, toward an uppermost layer of a device removes at least that uppermost layer and thereby exposes an underlying layer over, or comprising, a target area from which the site-specific, plan-view lamella is to be prepared, wherein the focused ion beam is in a face-on orientation in removing the uppermost layer to expose the underlying layer. In a preferred embodiment, the etch-assisting gas comprises methyl nitroacetate. In alternative embodiments, the etch-assisting gas is methyl acetate, ethyl acetate, ethyl nitroacetate, propyl acetate, propyl nitroacetate, nitro ethyl acetate, methyl methoxyacetate, or methoxy acetylchloride.

19 Claims, 14 Drawing Sheets

(56) References Cited

U.S. PATENT DOCUMENTS

| | | |
|---|---|---|
| 5,973,295 A | 10/1999 | Corbin et al. |
| 7,045,791 B2 | 5/2006 | Benas-Sayag et al. |
| 7,423,263 B2 | 9/2008 | Hong et al. |
| 8,524,606 B2 | 9/2013 | Charns et al. |
| 8,729,471 B2 | 5/2014 | Barbi et al. |
| 9,064,811 B2 | 6/2015 | Rue et al. |
| 2004/0082176 A1 | 4/2004 | Kane et al. |
| 2010/0181493 A1 | 7/2010 | Sudraud et al. |
| 2013/0118896 A1 | 5/2013 | Foster et al. |
| 2013/0248356 A1 | 9/2013 | Rue |
| 2013/0328246 A1 | 12/2013 | Wells et al. |
| 2014/0106559 A1 | 4/2014 | Anderson et al. |
| 2014/0357088 A1 | 12/2014 | Rue et al. |
| 2015/0209841 A1 | 7/2015 | Stahel et al. |
| 2015/0255248 A1* | 9/2015 | Boguslavsky ...... H01J 37/3056 204/192.34 |
| 2015/0279616 A1 | 10/2015 | Jiruse et al. |
| 2016/0126060 A1 | 5/2016 | Fuller et al. |
| 2016/0148783 A1 | 5/2016 | Lopour et al. |
| 2018/0166272 A1 | 6/2018 | Rue et al. |

\* cited by examiner

FACE-ON, GAS-ASSISTED ETCHING FOR PLAN-VIEW LAMELLAE PREPARATION

The present application claims priority from U.S. Provisional Patent Application No. 62/514,248, filed Jun. 2, 2017.

TECHNICAL FIELD

The present invention relates to focused-ion-beam (FIB)-based preparation of site-specific, plan-view TEM lamellae.

BACKGROUND

Transmission-electron-microscope (TEM) analysis of site-specific lamellae is becoming increasingly advantageous in early process development of microelectronic devices—particularly for failure analysis of device components. By "site-specific lamella" is meant an electron-transparent membrane having within the membrane a specific region that is to be examined under an electron microscope. Conventional methods of preparing site-specific lamellae (particularly in a plan-view orientation) from multilayered microelectronic devices are unfortunately deficient in many respects, including that these methods: (a) generally are capable of producing acceptably-electron-transparent lamellae of only relatively limited area dimensions (e.g., for reasons later herein detailed); and (b) often present challenges for end-pointing {i.e., identifying (or "pointing" to) which layer of a multilayered microelectronic device is the target layer containing the region of interest to which the process of edge-on FIB-based thinning should progress—while, on exposure of that target layer, the process of edge-on FIB-based thinning should cease (or "end")}.

More specifically, conventional methods of preparing site-specific, plan-view lamellae for TEM analysis often preclude process development engineers from, at least on a routine basis: (a) obtaining high quality lamellae (e.g., lamellae that are both largely free of analysis-interfering artifacts and have more-than-adequate electron transparency over sufficiently large areas); and (b) implementing processes amenable to straightforward end-pointing on exposure of, among layers of a multilayered microelectronic device, the target layer of interest—this latter preclusion also prevents process engineers from putting in place procedures for robust automation in end-pointing.

Failure analysis of a microelectronic device often involves failure analysis and fault isolation in a component integrated circuit (IC) device. In general, when the cause of a failure in an IC device is expected as originating from a defect in the metallization stack on the top of a device substrate, preparation of cross-sectional TEM specimens may often be identified as being particularly helpful for failure analyses. However, when the causative fault is indicated (e.g., from an electrical signature of a failure) as lying in the substrate (e.g., in dislocations or some other crystal defect), preparation of plan-view TEM specimens may often be seen as being particularly helpful for failure analyses. (1) R. Anderson and S. J. Klepies, *Practical aspects of FIB specimen preparation, with emphasis on semiconductor applications*, In: L. A. Giannuzzi & F. A. Stevie (ed's) Introduction to Focused Ion Beams—Instrumentation, Theory, Techniques and Practice. Springer Science, pp. 173-200, 192-193 (2005).

Regardless of the motivation for preparing a TEM specimen, however, a relatively straightforward, conventional "lift-out" method (either through ex-situ or in-situ means) is typically used to prepare a cross-sectional TEM specimen. In such lift-out method, a cross-sectional slice of material is lifted out of a work piece after the work piece has been milled perpendicularly to its surface, i.e., after cross-sectional cuts corresponding, respectively, to each side of the lift-out slice are milled through the work piece perpendicularly to the layers—with typically at least one cut, or often both cuts, being made in the form of a trench, e.g., possibly using a "stair step" milling algorithm—after a 0.5 to 1 μm thick metal line of platinum (Pt) or tungsten (W) has been deposited on the upper surface of the lift-out slice to protect it from ion beam damage. (2) L. A. Giannuzzi et al., *FIB lift-out specimen preparation techniques: ex-situ and in-situ methods*, In: L. A. Giannuzzi & F. A. Stevie (ed's) Introduction to Focused Ion Beams—Instrumentation, Theory, Techniques and Practice. Springer Science, pp. 201-228, 205-221 (2005). After being lifted out of the work piece, the slice is next fixed (e.g., typically yet in a vertical orientation) onto a TEM grid, where it may be further thinned (e.g., to at least an acceptable level of electron transparency) from either side, e.g., using additional FIB milling (again perpendicularly to the work piece's internal layers) or using low-voltage ion milling at a grazing incidence. See, e.g., FIGS. 2-4 and associated text in "Background of the Invention" section of (3) U.S. Pat. No. 7,423,263 (the '263 patent—issued Sep. 9, 2008) to Liang Hong et al., "*Planar view sample preparation*" (Assignee: FEI Company).

In a conventional method for preparing a plan-view lamella, in contrast, a wedge or chunk is first cut from work piece material by FIB milling. Standard gallium ion (Ga$^+$) FIB milling is commonly used to cut the wedge in from the work piece, although such wedge-defining milling may proceed relatively slowly and require acceptance of some embedding in the wedge of contaminant Ga$^+$ ions.

After this wedge is removed from the work piece, its orientation is tilted by 90°—possibly through rotating a carrier to which the wedge is mounted, e.g., so that previously horizontal wedge layers are now oriented vertically and potentially parallel to the ion beam column. See also FIGS. 10-12 and associated text of (3) U.S. Pat. No. 7,423,263; see also panels (b) to (d) of FIG. 3 of (4) J. Mayer, L. A. Giannuzzi, T. Kmino, and J. Michael, *TEM sample preparation and FIB-induced damage*, MRS [Materials Research Society] Bulletin, Vol. 32, pp. 400-407 (May 2007). The re-oriented wedge is then thinned, e.g., "bulk thinned" using FIB milling edge-on to the wedge's layers, to generate a plan-view lamella. Because the edge-on milling removes all material along the beam axis, the resultant lamella comprises a thinned section extending from the top of the lamella to the bottom of the lamella, with thicker borders on one or both sides.

Edge-on FIB milling alone, however, cannot solely be relied on to prepare a plan-view lamella consisting of a target layer containing the region of interest and having an acceptable level of planarity. A process of slow and repetitive, glancing-angle cleaning in an FIB system—accompanied by many FIB system adjustments (e.g., for scan rotation, z-dimension depth, ion column tilt, or pixel overlap)—is often required to remove artifacts or to address areas of varying hardness on a lamella. In addition, simply correctly identifying and selecting the target layer containing the region of interest (i.e., identifying the previously horizontal layer within a re-oriented wedge from which a plan-view lamella is to be prepared) is often challenging when using this conventional method for preparing a plan-view lamella. Considerable effort may be wasted on completing repetitive, glancing-angle cleaning of a presumed target layer only to learn subsequently that the cleaned layer had been misidentified and is in fact not the target layer.

How thinly a TEM specimen may be milled using a conventional method is largely limited by how closely the line of FIB milling on one side of the TEM specimen may realistically approach the line of FIB milling on the other side of the specimen—without the specimen (i.e., the nascent or intended lamella) voiding the specimen-preparation effort by bending, curling, shrinking, or otherwise warping. If a specimen that is being bulk-thinned through FIB milling does bend, curl, or otherwise warp during FIB milling, the ion beam most likely will destroy the specimen or render it essentially unusable for TEM analysis. Because edge-on thinning produces a thin center section that extends from the top of the lamella to the bottom of the lamella, the lamella lacks a thicker support along the top and bottom to resist warping.

Accordingly, in order for edge-on FIB milling of a specimen from a re-oriented wedge of a multilayered microelectronic device to generate a plan-view lamella that is sufficiently thin for successful TEM analysis (e.g., often a thickness of less than about 100 nm may be required for a lamella to have acceptable electron transparency), the proclivity of the specimen (particularly a larger-area specimen) to bend, curl, or otherwise warp while being thinned must be forestalled. See, regarding 100 nm thickness of lamella, (5) U.S. Pat. Appl. Pub. No. 20160126060 (the '060 patent application—published May 5, 2016) to Fuller et al., "Endpointing for focused ion beam processing" (Applicant for parent PCT Application: FEI Company) ("[0003] . . . While a SEM [scanning electron microscope] can observe a feature on a thick work piece, to observe a sample on a TEM, it needs to be thinned to less than 100 nm so that electrons will travel through the sample."). As used herein, a sample or specimen is an object extracted from a work piece. A lamella is a thin, electron-transparent membrane form of a sample.

Although the difficulty of preventing such bending, curling, or warping will generally increase as a lamella becomes larger in area and thinner in depth, a lamella of a larger area is typically preferred for precise TEM analysis, and some TEM analysis may even require that a lamella be prepared having a thickness of less than about 20 nm. See (6) U.S. Pat. Appl. Pub. No. 20130328246 (the '246 patent application—published Dec. 12, 2013) to Wells et al., "Lamella creation method and device using fixed-angle beam and rotating sample stage" (Assignee: FEI Company) ("[0009] . . . Lamellae are typically less than 100 nm thick, but for some applications a lamella must be considerably thinner. With advanced semiconductor fabrication processes at 30 nm and below, a lamella needs to be less than 20 nm in thickness in order to avoid overlap among small scale structures.").

The proclivity of a plan-view specimen prepared according to the above-summarized conventional method to bend, curl, or otherwise warp often increases to an unacceptable level when the TEM specimen's area of electron transparency (again, which typically has a thinness of less than about 100 nm) is roughly larger than about 5 µm×5 µm=about 25 µm$^2$ (or, in some cases, simply larger than about 2 µm×2 µm=about 4 µm$^2$). As a result, a plan-view lamella being prepared from a re-oriented wedge taken from a multilayered microelectronic device using the above-noted conventional method is typically limited to a size roughly less than 5 µm×5 µm=about 25 µm$^2$ (and, in some cases, simply less than about 2 µm×2 µm=about 4 µm$^2$).

In addition, preparation of a site-specific, plan-view lamella (e.g., one corresponding to a target layer of a multilayered microelectronic device) using the above-noted conventional method is also not amenable to straightforward end-pointing (nor to automation in end-pointing). This is so in part because, for example, identifying (or "pointing" to) which layer of a multilayered microelectronic device is the target layer containing the region of interest to which the process of edge-on FIB milling should progress—while, on exposure of that target layer, the process should cease (or "end")—is often inordinately difficult when using the above-noted conventional method for plan-view lamella preparation.

For example, a key identifying characteristic of an individual layer—its planar-oriented, lithography-generated circuit pattern—may often need to be estimated by an expert only from cut circuit lines along the exposed side planes of a re-oriented wedge. But observing less-than-clear, edge-on views of some of the possibly 35 or more sliced layer edges of a microelectronic device may often lead an expert to identify a specific layer only tentatively. Nonetheless, an expert will very likely be stuck with relying on such less-than-clear, edge-on views of cut circuit lines because, for example, unobstructed views of planar-oriented circuit patterns of individual layers may not be available during most of an edge-on FIB milling process (i.e., the bulk thinning process).

Furthermore, even if edge-on FIB milling were fortuitously to progress to the correct target layer, subsequently identifying certain sections of the target layer's circuit pattern often presents difficulties. This is so in part because planar surfaces (often marginally planar) exposed through such edge-on FIB milling (even after repetitive, glancing-angle cleaning) often are, alternatively: (i) damaged by embedded $Ga^+$ ions (e.g., as may result from an ion beam being directed at an angle that is not optimized for surface cleaning—possibly through a miscalculated compensation for an expected Gaussian shape of the ion beam); (ii) yet obstructed by curtaining artifacts (i.e., by striations or veils that may result, e.g., where materials having a low sputtering yield block faster sputtering yield materials); or (iii) characterized by an exposed circuit pattern that shares many commonalities with a circuit pattern of an adjacent layer (e.g., as is often the case for 3D-NAND memory devices)—so that unequivocally distinguishing sections of a target layer's circuit pattern from those of an adjacent layer may yet remain challenging.

At least for these above-noted reasons, it would be desirable to provide a FIB-based method for preparing a site-specific, plan-view lamella of a region of interest in a multilayered microelectronic device wherein the method both allows for the routine preparation of lamellae of an area larger than at least about 100 µm$^2$ (e.g., larger than at least about 10 µm×10 µm) and is clearly amenable to straightforward end-pointing (including automation in end-pointing).

SUMMARY

An object of the invention is to provide methods and apparatuses for fabricating plan view lamellae, as well as to provide plan view lamellae.

A method of fabricating, from a sample extracted from a semiconductor work piece, a lamella including an electron-transparent portion including a region of interest, the semiconductor work piece having multiple layers parallel to its surface, comprises directing a focused ion beam toward the work piece to cut the sample from the work piece; directing a focused ion beam oriented parallel to multiple layers toward the sample to thin the sample to form a lamella;

providing an etch-assisting gas at the surface of the lamella; and directing a focused ion beam oriented perpendicularly to the multiple layers toward the lamella to thin in the presence of the etch-assisting gas a portion of the lamella to produce the electron-transparent portion including the region of interest.

In some embodiments, ion beam images are used to determine when to stop thinning the lamellae. In some embodiments, methods of removing curtaining and other artifacts are provided.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1A:
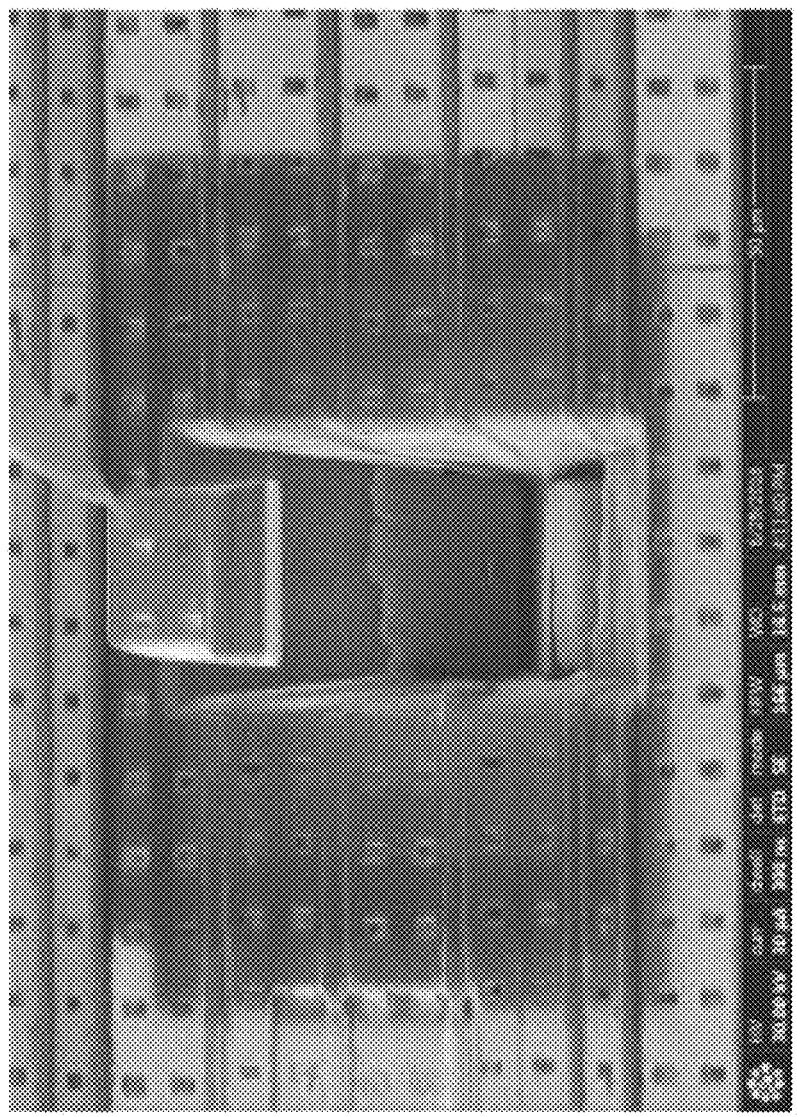
FIG. 1A is an image from a scanning electron microscope (SEM) of a probe being used to move a "lift out" wedge specimen from a microelectronic device—such a "lift out" wedge or chunk is similarly illustrated in panel (a) of FIG. 3 of reference (4).

One embodiment or implementation is directed to a FIB-based method for preparing a site-specific, plan-view lamella from a multilayered microelectronic device through successive removals of an existing uppermost layer from the device by face-on, gas-assisted etching. Another embodiment or implementation is directed to a plan-view lamella that is prepared using this FIB-based method; the planarity of the plan-view lamella so prepared may be enhanced in such an embodiment or implementation. Yet another embodiment or implementation is directed to a related FIB-based method of artifact removal from a target area of an exposed layer of a device. A further embodiment or implementation is directed to a method of automatically end-pointing—using an image-based criterion or a counting means or methodology—the process of successively removing an existing uppermost layer from a device.

The use of the face-on milling using an MNA-related gas (defined below) for delayering a plan view lamella facilitates planarize and maintenance of the planarity of the lamella as it is thinned. In the conventional approach, a user has to make very careful adjustments to the stage tilt, scan rotation, and pattern positioning to achieve a cross-sectional cut face that is parallel to the metal layers of the sample. In practice, it is nearly impossible to achieve a perfect coincidence between the plane of the cut face and the intrinsic planes of the metal layers on the sample. Using the methods described herein, however, the milling is almost self-planarizing. It is much easier to establish planarity, and the various operational parameters such as stage tilt, scan rotation, pattern placement are much more forgiving. Also, it is easier to observe layer transitions in real time from the live FIB image during milling. Because the image is face-on, the user can see the features in the exposed face. This makes end pointing easier, and allows automating the endpointing at a particular layer based on feedback from the live FIB image. In the conventional approach, the user receives almost no feedback from the FIB image because the image of the sample is edge-on. All images related to targeting and endpointing in the prior art method, therefore, has to come from the SEM imaging.

The face-on lamella delayering processes can be used at very low energies: 5-12 keV is common, and 2 keV is becoming more common. In some embodiments, ion energies below 1 keV are used. Low ion energies are desirable because ions impacting the surface disrupt the crystal structure, creating an amorphous damage layer. Reduced beam energy reduces the amorphous damage layers. In conventional edge-on thinning, low beam energies reduce the image resolution, so pattern placement is difficult because a user cannot see the sharp edge of features very clearly. In face-on milling, low ion energy processing is possible because a user can view the sample over a large XY area at low energies, and even though the imaging resolution is poor, the patterning placement is very forgiving. A user can raster over the whole sample, and even though the image is fuzzy, a user would still be able to determine that the beam is hitting the approximate target area.

The drawbacks of the prior art are overcome through the use of Dx gas, i.e., methyl nitroacetate (MNA) or an MNA-like gas, as a precursor gas in modified charged particle beam processes, and, in particular, as a precursor gas in FIB-based method for lamellae preparation from multilayered microelectronic devices through face-on, gas-assisted etching. In particular, innovations disclosed herein provide, inter alia, FIB-based method, particularly plasma FIB (PFIB)-based method, for site-specific, plan-view lamellae preparation from multilayered microelectronic devices through face-on, gas-assisted etching, wherein the method is both amenable to straightforward end-pointing (including automation in end-pointing) and allows for the routine preparation of lamellae (including largely curtain-free lamellae) of an area larger than at least: about 100 $\mu m^2$; about 225 $\mu m^2$; about 400 $\mu m^2$; about 625 $\mu m^2$; about 900 $\mu m^2$; about 1225 $\mu m^2$; about 1600 $\mu m^2$; about 2025 $\mu m^2$; or about 2500 $\mu m^2$ (e.g., larger than at least, respectively: about 10 $\mu m \times 10$ $\mu m$; about 15 $\mu m \times 15$ $\mu m$; about 20 $\mu m \times 20$ am; about 25 $\mu m \times 25$ $\mu m$; about 30 $\mu m \times 30$ $\mu m$; about 35 $\mu m \times 35$ $\mu m$; about 40 $\mu m \times 40$ $\mu m$; about 45 $\mu m \times 45$ $\mu m$; or about 50 $\mu m \times 50$ $\mu m$)—or any other approximate product area resulting from the multiplication of any of the individual breadth or width dimensions noted in the preceding parentheses, as well as a breadth or width dimension of 5 $\mu m$ (as long as the approximate product area is equal to or larger than about 100 $\mu m^2$). In summary, each approximate area from larger than at least about 100 $\mu m^2$ to larger than at least about 2500 $\mu m^2$ (including all approximate areas in increments of 25 $\mu m^2$ there-between) is hereby encompassed as an approximate area for which lamellae (including largely curtain-free lamellae) may be routinely prepared according to FIB-based method disclosed herein.

Use of MNA (or MNA-related chemical) as a precursor gas in FIB-mediated planar deprocessing of semiconductor devices is disclosed in (7) U.S. Pat. No. 9,064,811 (the '811 patent—issued Jun. 23, 2015) to Chad Rue et al., *Precursor for planar deprocessing of semiconductor devices using a focused ion beam*" (Assignee: FEI Company), which herein is incorporated by reference in its entirety. "MNA-related chemical" includes (nonexclusively) methyl acetate, ethyl acetate, ethyl nitroacetate, propyl acetate, propyl nitroacetate, nitro ethyl acetate, methyl methoxyacetate, methoxy acetylchloride, and similar chemical compounds containing short-chain hydrocarbons joined to acetate, nitro, or nitroacetate groups such that: (a) use of the chemical results in moderate vacuum chamber pressures in the range of about $2 \times 10^{-6}$ to about $5 \times 10^{-5}$ mbar [i.e., about $1.5 \times 10^{-6}$ to about $3.75 \times 10^{-5}$ Torr] while the precursor gas is flowing (and with the baseline chamber pressure when the chemical compound is not flowing being in the range of about $1 \times 10^{-7}$ to about $1 \times 10^{-6}$ mbar [i.e., about $7.5 \times 10^{-8}$ to about $7.5 \times 10^{-7}$ Torr]) for convenient delivery of the chemical into the FIB vacuum chamber (for a FIB implementation using MNA-related chemical); and (b) the chemical has an oxidizing capacity toward the sample, or toward contaminant molecules adsorbed onto the sample surface.

Accordingly, described herein are FIB-based methods for site-specific, plan-view lamellae preparation from multilayered microelectronic devices through face-on, gas-assisted etching, wherein the method is both amenable to straightforward end-pointing (including automation in end-pointing) and allows for the routine preparation of lamellae (including largely curtain-free lamellae) of an area larger than at least about 100 $\mu m^2$ to an area larger than at least about 2500 $\mu m^2$ (including all approximate areas in increments of about 25 $\mu m^2$ there-between) that are highly suitable for TEM analyses. Also described is a method for removal of curtain artifacts in the preparation of largely curtain-free lamellae.

TABLE 1

Key Abbreviations

| Abbreviation | Appositive |
|---|---|
| Dx | methyl nitroacetate precursor gas |
| FIB | focused ion beam |
| HAADF | high-angle annular dark-field |
| IC | integrated circuit |
| MNA | methyl nitroacetate |
| PFIB | plasma focused ion beam |
| SE | secondary electron |
| SEM | scanning electron microscope |
| STEM | scanning TEM |
| TEM | transmission electron microscope |

In some embodiments, a sample in the form of a wedge or chunk is typically first cut from a work piece by FIB milling as described above. The wedge or check is typically bulk thinned to form a lamella, and then face-on milling with an etching gas is used to thin or delayer the lamella until the desired thickness is achieved and the layer to be examined is exposed in the electron-transparent lamella. While face-on, gas assisted etching provides advantages in thinning to the desired final thickness, face-on milling is not well suited for removing the thick layers often encountered in preparing a plan view lamella. There are often one or more thick metal layers, often as thick as 0.5 um to 1.5 um, on the top of a semiconductor substrate. The thick layers can be composed of various materials, such as aluminum, polyimide, etc., and may have uneven, non-planar topography, making these layers unsuitable for top-down, etch-gas assisted focused ion beam thinning. It is convenient to remove these layers with conventional, edge-on milling, before switching to the face-on, gas-assisted techniques described herein as the final desired thickness is approached and the target layer is near to being exposed.

To perform the edge-on, bulk thinning, after the wedge is removed from the work piece, the wedge is rotated about 90° by, for example, rotating a carrier to which the wedge is mounted, so that previously horizontal wedge layers are now oriented vertically and approximately parallel to the ion beam column. The re-oriented wedge is then "bulk thinned" using FIB milling edge-on to the wedge's layers to remove the thick metal layer or other material over an identified target layer that is to be imaged on a TEM.

The lamella can be imaged periodically using an SEM until layers suitable for face-on milling, e.g., planarized layers with Cu metallurgy and a layer thickness of less than about 500 nm or less are exposed. In the various embodiments of face-on milling described herein, it will be understood that face-on milling may be preceded by edge-on milling to remove thick layers.

After layers suitable for face-on milling are exposed, the lamella is rotated to be approximately normal to the ion beam and lamella fabrication continues by (a) directing an etch-assisting gas toward the uppermost layer over the target area; (b) directing a focused ion beam toward the uppermost layer over the target area, thereby removing the uppermost layer and exposing an underlying layer over, or comprising, the target area; and (c) repeating steps (a) and (b) until the exposed underlying layer is one comprising the target area, wherein said exposed underlying layer comprising the target area then defines the plan-view lamella; in which: the etch-assisting gas comprises at least one chemical or more selected from a group consisting of methyl nitroacetate, methyl acetate, ethyl acetate, ethyl nitroacetate, propyl acetate, propyl nitroacetate, nitro ethyl acetate, methyl methoxyacetate, and methoxy acetylchloride; and the focused ion beam mills away the uppermost layer in a face-on orientation.

In some embodiments, the method includes performing multiple repetitions of the steps of providing the etch-assisting gas at the surface of the lamella; and directing a focused ion beam oriented perpendicularly to the multiple layers toward the lamella to thin in the presence of the etch-assisting gas a portion of the lamella. An ion beam image of the lamella is formed after at least one of the repetitions; and from the image, the user determined when to cease the repetitions. For example, the user could determine to cease the repetitions when the region of interest is visible in the ion beam image. Alternatively, the user could determine from the image which layer is exposed and how many additional layers need to be removed to reach the layer of interest. The user could then count each intervening layer is removed and cease the repetition when the determined number of layers have been removed.

In related method, described are: focused ion beam originating from a plasma focused ion beam source; ions of the focused ion beam being selected from a group consisting of: Xe+, Ar+, Kr+, O+, O2+, N+, N2+, NO+, and NO2+; focused ion beam operating during the removing at an acceleration voltage ranging from about 2 keV to about 30 keV, or ranging from about 5 keV to about 12 keV; etch-assisting gas chemical being or comprising methyl nitroacetate or other MNA-related gas; exposed underlying layer being largely curtain-free; square area having an electron transparency suitable for TEM analyses within the target area both being larger than at least about 5 µm by 5 µm and being within an overall area of electron transparency suitable for such TEM analyses that is larger than at least about 100 µm2, in which, for example, layer thickness within the square area is largely throughout less than about 100 nm, or largely throughout less than about 20 nm.

Some embodiments further include removal of an exposed backside metal layer underlying the target area: re-orienting the device so that the focused ion beam is directed face-on to the device's backside and, after the re-orienting, the exposed backside metal layer is over the target area; optionally, directing an etch-assisting gas toward the exposed backside metal layer; directing a focused ion beam toward the exposed backside metal layer, thereby removing the exposed backside metal layer; in which: the etch-assisting gas, if used for removal of an exposed backside metal layer, comprises at least one chemical or more selected from a group consisting of xenon difluoride, DE, methyl nitroacetate, methyl acetate, ethyl acetate, ethyl nitroacetate, propyl acetate, propyl nitroacetate, nitro ethyl acetate, methyl methoxyacetate, and methoxy acetylchloride; and the focused ion beam mills away the exposed backside metal layer in a face-on orientation.

In some embodiments or implementations, plan-view lamella prepared from a multilayered microelectronic device by a process is described, the process comprising the steps of: (a) defining a target area in a layer below an uppermost layer of the device, wherein the target area is to be encompassed by the plan-view lamella; (b) directing an etch-assisting gas toward the uppermost layer over the target area; (c) directing a focused ion beam toward the uppermost layer over the target area, thereby removing the uppermost layer and exposing an underlying layer over, or comprising, the target area; (d) repeating steps (b) and (c) until the exposed underlying layer is one comprising the target area, wherein said exposed underlying layer comprising the target area then defines the plan-view lamella; in which: the etch-assisting gas comprises at least one chemical or more selected from a group consisting of methyl nitroacetate, methyl acetate, ethyl acetate, ethyl nitroacetate, propyl acetate, propyl nitroacetate, nitro ethyl acetate, methyl methoxyacetate, and methoxy acetylchloride; and the focused ion beam mills away the uppermost layer in a face-on orientation. For plan-view lamella prepared from a multilayered microelectronic device by related process, described are: exposed underlying layer comprising the target area being largely curtain-free; and square area having an electron transparency suitable for TEM analyses within the target area both being larger than at least about 5 µm by 5 µm and being within an overall area of electron transparency suitable for such TEM analyses that is larger than at least about 100 µm2, in which, for example, layer thickness within the square area is largely throughout less than about 100 nm, or largely throughout less than about 20 nm.

A plan view lamella prepared by the above-process is structurally different from lamella prepared by prior art processes. The plan view lamella comprises a thinner, electron transparent center portion surrounded by a thicker frame. While the thinned, electron-transparent center portion is typically less than 100 nm, the edges of the frame may be thicker than about 200 nm, thicker than about 400 nm, thicker than about 500 nm, and may be between 1 m and several microns. The edges are typically at least twice as thick as the center, electron-transparent portion, at least three times as thick as the center, electron-transparent portion, or at least four times as thick as the center, electron-transparent portion. For example, the electron-transparent area may have a thickness of less than 100 nm and be essentially surrounded by a frame having a thickness at least 100 nm thicker than the thickness of the electron transparent region. By essentially surrounded is meant preferably surrounded on all sides, although there may be gaps in the frame that have minimal impact of the mechanical strength and resistance to warping.

In some embodiments or implementations, method of curtain artifact removal from a target area of an exposed layer is described, the method comprising: (a) defining a target area containing a curtain artifact on an exposed layer; (b) directing an etch-assisting gas toward the target area; and (c) directing a focused ion beam toward the target area, thereby removing the curtain artifact from the target area; in which: the etch-assisting gas comprises at least one chemical or more selected from a group consisting of methyl nitroacetate, methyl acetate, ethyl acetate, ethyl nitroacetate, propyl acetate, propyl nitroacetate, nitro ethyl acetate, methyl methoxyacetate, and methoxy acetylchloride; and the focused ion beam mills away the curtain artifact in a face-on orientation. In related method, described are: focused ion beam originating from a plasma focused ion beam source; ions of the focused ion beam being selected from a group consisting of: Xe+, Ar+, Kr+, O+, O2+, N+, N2+, NO+, and NO2+; focused ion beam operating during the removing at an acceleration voltage ranging from about 2 keV to about 30 keV, or ranging from about 5 keV to about 12 keV; and etch-assisting gas chemical being or comprising methyl nitroacetate. The curtain artifact is removed by planarizing the lamella surface.

In other embodiments or implementations, method of automatically end-pointing a layer removal process from a multilayered microelectronic device through face-on, gas-assisted etching with a charged particle beam is described, the method comprising: (a) defining an image-based criterion for an uppermost layer that specifies when the layer removal process is complete and the layer removal process is to end; (b) imaging the uppermost layer; (c) automatically evaluating the uppermost layer using the criterion to determine if the criterion is met and the layer removal process ends; (d) if the criterion is not met, repeatedly directing that steps (e), (f), (g), and (h) be repeated until the criterion is met and the layer removal process ends; (e) directing an etch-assisting gas toward the uppermost layer; (f) directing a focused ion beam toward the uppermost layer, thereby removing the uppermost layer; (g) imaging the uppermost layer; (h) automatically evaluating the uppermost layer using the criterion to determine if the criterion is met and the layer removal process ends; in which: the etch-assisting gas comprises at least one chemical or more selected from a group consisting of methyl nitroacetate, methyl acetate, ethyl acetate, ethyl nitroacetate, propyl acetate, propyl nitroacetate, nitro ethyl acetate, methyl methoxyacetate, and methoxy acetylchloride; and the focused ion beam mills away the uppermost layer in a face-on orientation.

In other embodiments or implementations, method of automatically end-pointing a layer removal process from a multilayered microelectronic device through face-on, gas-assisted etching with a charged particle beam is described, the method comprising: (a) setting or entering an integer number N corresponding to a number of layers to be removed in the layer removal process; (b) automatically determining if N minus a counter of layers removed equals zero; (c) if N minus a counter of layers removed equals zero, ending the layer removal process; (d) if N minus a counter of layers removed does not equal zero, repeatedly directing that steps (e), (f), (g), and (h) be repeated until N minus a counter of layers removed equals zero and the layer removal process ends; (e) directing an etch-assisting gas toward the uppermost layer; (f) directing a focused ion beam toward the uppermost layer, thereby removing the uppermost layer; (g) increasing a counter of layers removed by 1; (h) automatically determining if N minus the counter of layers removed equals zero and the layer removal process ends; in which: the etch-assisting gas comprises at least one chemical or more selected from a group consisting of methyl nitroacetate, methyl acetate, ethyl acetate, ethyl nitroacetate, propyl acetate, propyl nitroacetate, nitro ethyl acetate, methyl methoxyacetate, and methoxy acetylchloride; and the focused ion beam mills away the uppermost layer in a face-on orientation.

Not all aspects described above will be present in every embodiment or implementation of the invention.

FIG. 1A is an image from a scanning electron microscope (SEM) of a probe being used to move a "lift out" wedge specimen from a microelectronic device.

Figure 1B:
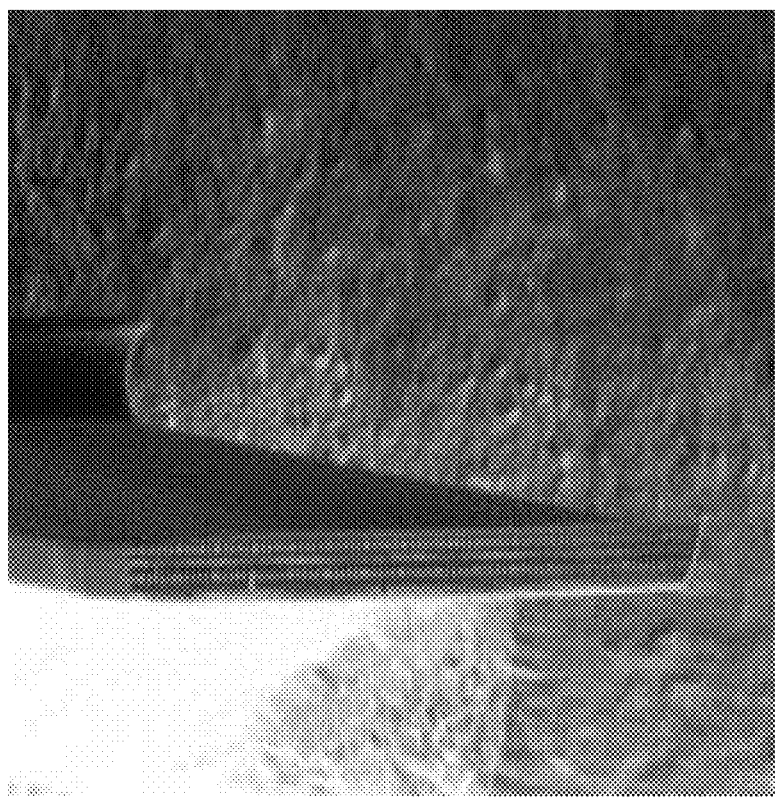
FIG. 1B is a SEM image of a lamella prepared from a multilayered microelectronic device, wherein layers of the lamella are vertically oriented after the lamella has been bulk thinned through edge-on FIB milling.

FIG. 1B is a SEM image of a sample prepared from a multilayered microelectronic device wherein layers of the sample are vertically oriented after the sample has been bulk thinned through edge-on FIB milling.

Figure 1C:
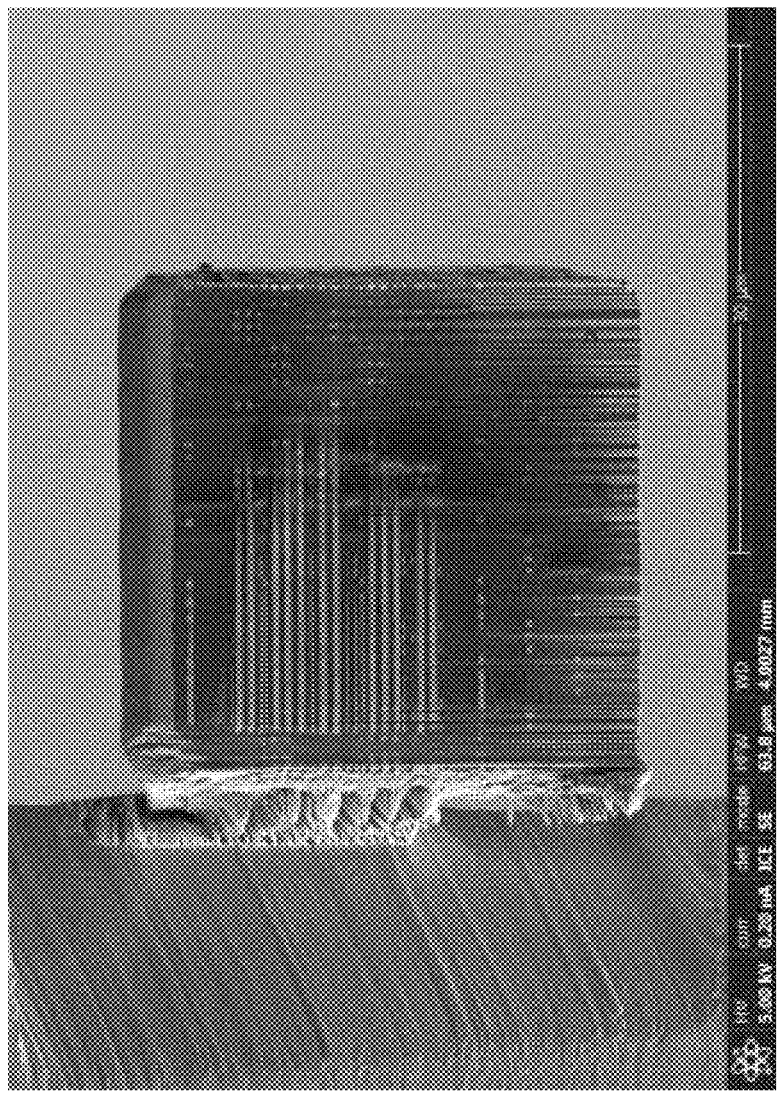
FIG. 1C is a SEM image of a similar lamella, i.e., a lamella including a square-shaped IC device, isolated from a larger multilayered microelectronic device and mounted to a grid.

FIG. 1C is a SEM image of a square-shaped IC device isolated at least in part by FIB milling from a larger multilayered microelectronic device and mounted to a grid. Vertical curtains, veils or striations (i.e., curtain artifacts from FIB milling) are visible on the front face of the IC device (the bright horizontal lines represent metal lines of the IC device).

Figure 1D:
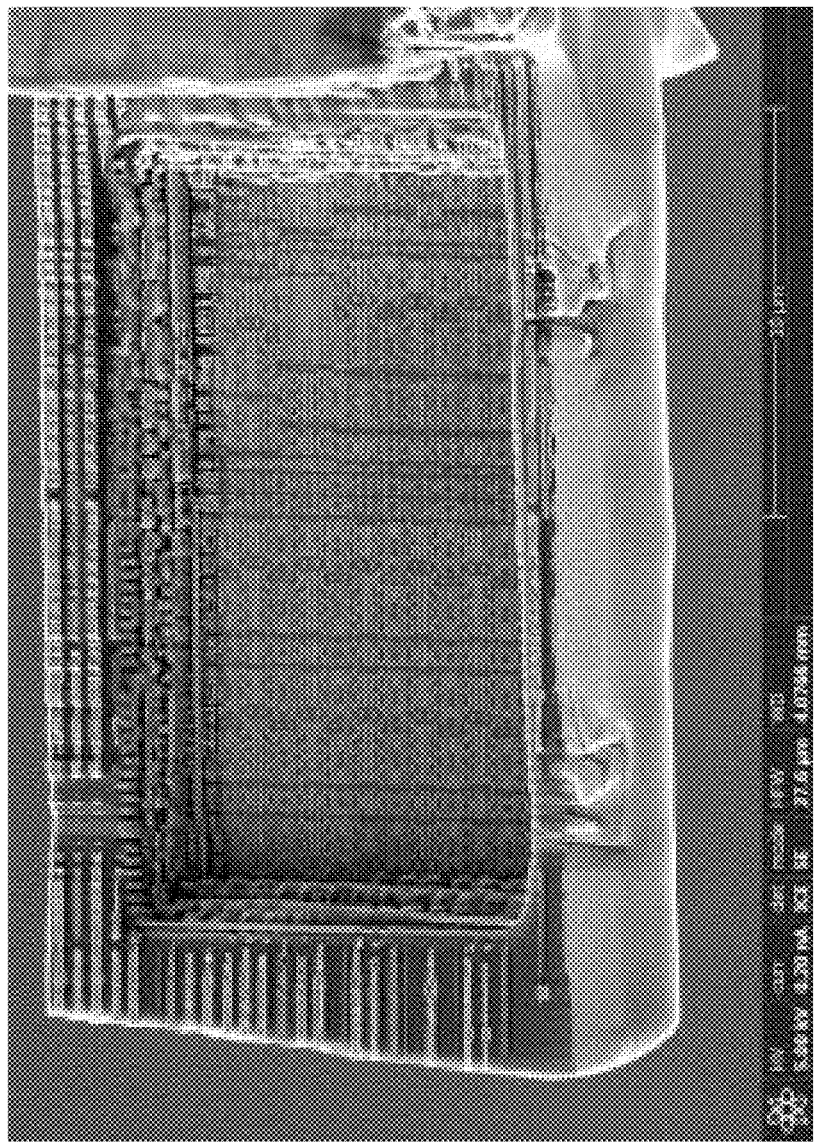
FIG. 1D is a SEM image that displays an exposed planar layer of an IC device like that of FIG. 1C after the successive removals of layers that previously covered the currently exposed planar layer were accomplished through PFIB-based, face-on, gas-assisted etching using MNA as a precursor gas; IC device layers remain beyond the peripheries of the box-mill area frame and support the exposed planar layer; in order in part to enhance surface planarity, curtain artifacts were also removed from the exposed planar layer through PFIB-based, face-on, gas-assisted etching using MNA as a precursor gas.

FIG. 1D is a SEM image that displays an exemplary exposed planar layer of an IC device like the IC device of FIG. 1C after the successive removals of layers previously covering the currently exposed planar layer were accomplished through PFIB-based, face-on, gas-assisted etching using MNA as a precursor gas. The currently exposed uppermost layer is "expansive" when judged by typical plan-view lamella preparation standards, i.e., it has an area larger than 15 µm×35 µm. Furthermore, surface planarity over this expansive area is enhanced through removal of curtain artifacts with PFIB-based, face-on, gas-assisted etching using MNA as a precursor gas. Advantageously, the face-on, gas-assisted etching has generated a lamella that— for the prevention of bending, curling, or warping—is supported on four sides. While the thinned, electron-transparent center portion is typically less than 100 nm, the edges of the frame may be thicker than about 200 nm, thicker than about 400 nm, thicker than about 500 nm, and may be between 1 µm and several microns. The edges are typically at least twice as thick as the center, electron-transparent portion, at least three times as thick as the center, electron-transparent portion, or at least four times as thick as the center, electron-transparent portion. Etching was carried out using a Xe+ plasma FIB beam at an acceleration voltage of 2-30 keV, or 5-12 keV more commonly, and a current density of 0.5-20 pA/µm2, or 2-10 pA/µm2 more commonly, with a dwell time of 100 nsec, a 65% pixel overlap, and a chamber pressure (with the precursor gas valve open) of 1-2×10-5 mbar. In the removal of thicker upper layers {i.e., other than the top one or two metal layers, which each may be several micrometers thick; these particularly thick top one or two metal layers may be removed either by using mechanical grinding/polishing or by using conventional cross-sectional FIB milling (in situ), e.g., with the sample oriented as in FIG. 1B, before re-orientation of the sample to be normal to the FIB for further delayering—possibly with, e.g., curtaining removal—using Dx gas}, etching was typically carried out at an acceleration voltage of: 30 keV (for metal layers having a thickness of 0.2 to 0.5 am); 12 keV (for layers having a thickness of 0.1 to 0.2 am); or 5 keV (for metal layers thinner than ~0.1 μm). Under these conditions, a typical layer within the region of box milling was removed within 2 to 5 minutes. However, metal layers that are thicker than ~0.5 μm are usually not well-suited for delayering using Dx (or MNA-related chemical) as a precursor gas.

Figure 1E:
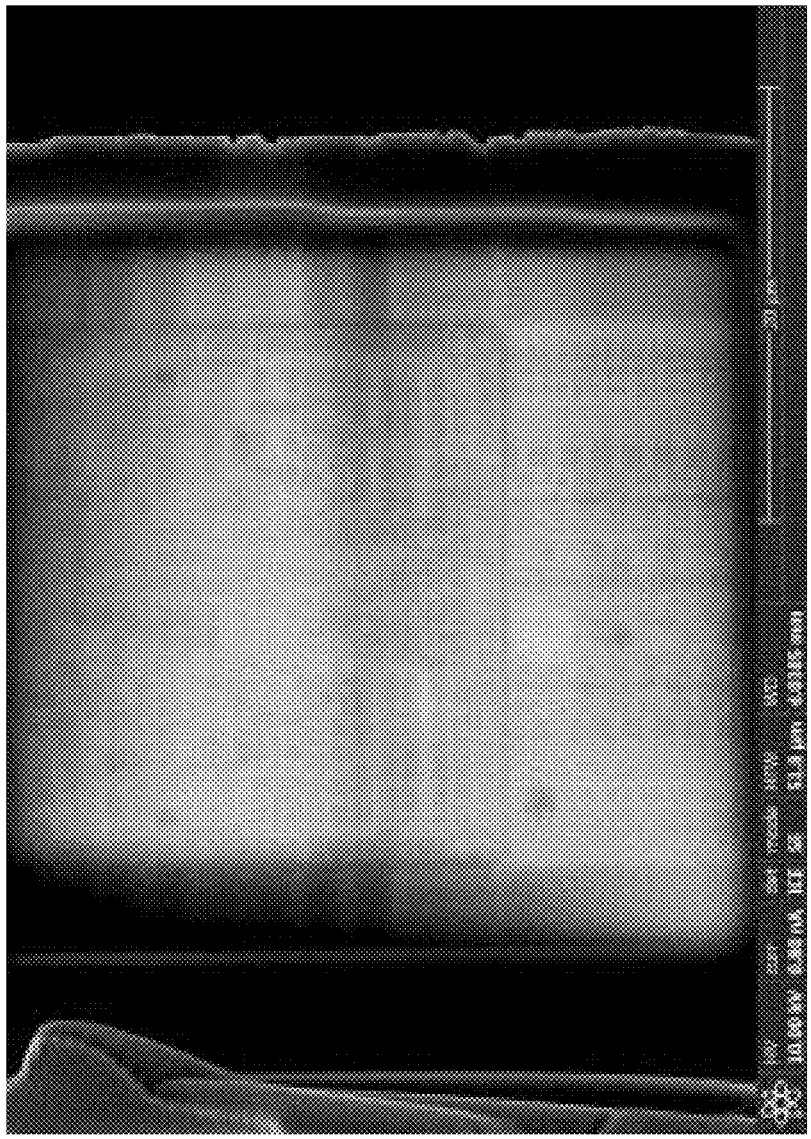
FIG. 1E is a SEM image of the backside of a microelectronic device after "silicon thinning" on that backside of an area larger than about 25 $\mu m \times 25$ $\mu m$=about 625 $\mu m^2$ was accomplished through PFIB-based, face-on etching, in this case, without using a precursor gas.

FIG. 1E is a SEM image of the backside of a plan-view lamella of a microelectronic device after "silicon thinning" on that backside of an area larger than about 25 μm×25 μm=about 625 μm² was accomplished through xenon (Xe+) PFIB-based, face-on etching without using a precursor gas. An acceleration voltage of 5 keV was used. For some embodiments or implementations, xenon difluoride (XeF2) gas or another halogenated etching gas may be used intermittently as a precursor gas to accelerate the rate of silicon removal. For other embodiments or implementations, MNA (or MNA-related chemical) may be used as a precursor gas in face-on, gas-assisted etching of microelectronic devices for layer removal from the backside (e.g., after appropriately re-orienting the device within a FIB system).

Figure 2A:
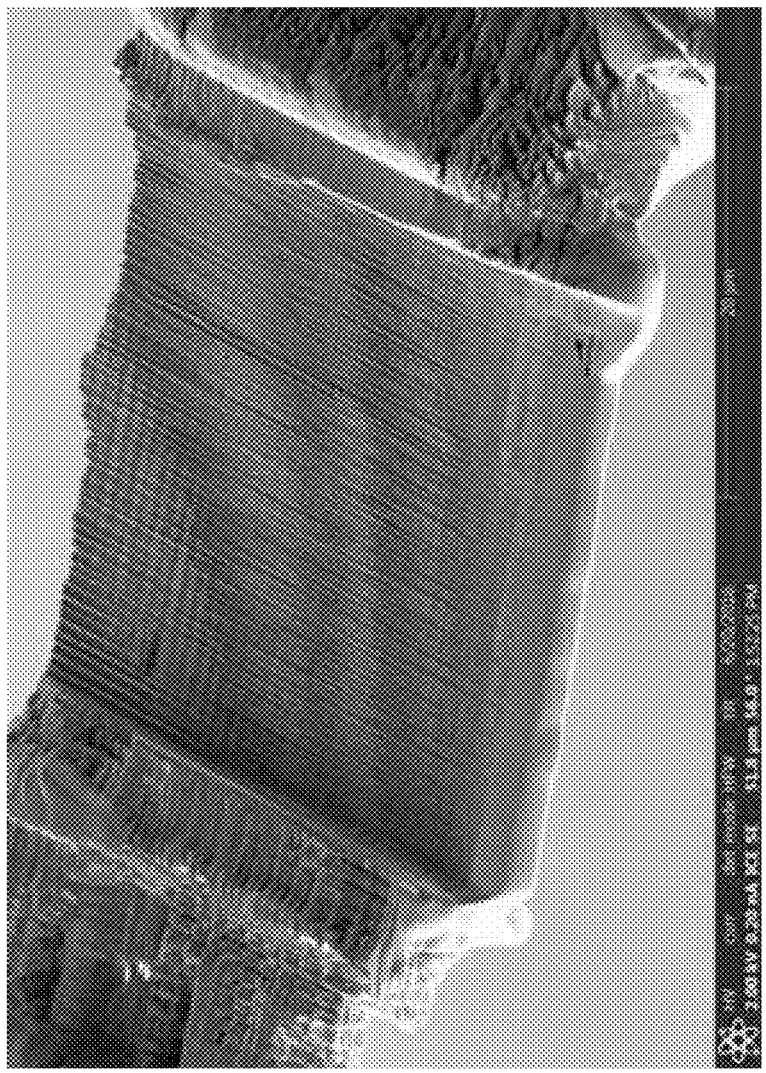
FIG. 2A is a SEM image that displays a nascent plan-view lamella (of an area larger than 20 $\mu m \times 20$ $\mu m$=about 400 $\mu m^2$) of a multilayered microelectronic device.

FIG. 2A is a SEM image that displays a nascent plan-view lamella of a multilayered microelectronic device. The lamella was prepared conventionally, i.e., via top-down (or edge-on) FIB milling (notice that, as is typical for conventional lamella preparation, the nascent plan-view lamella does NOT have support frames on all four sides, but only on two sides). The surface area of the nascent plan-view lamella is larger than about 20 μm×20 μm=about 400 μm2 but is extensively covered with curtain artifacts.

Figure 2B:
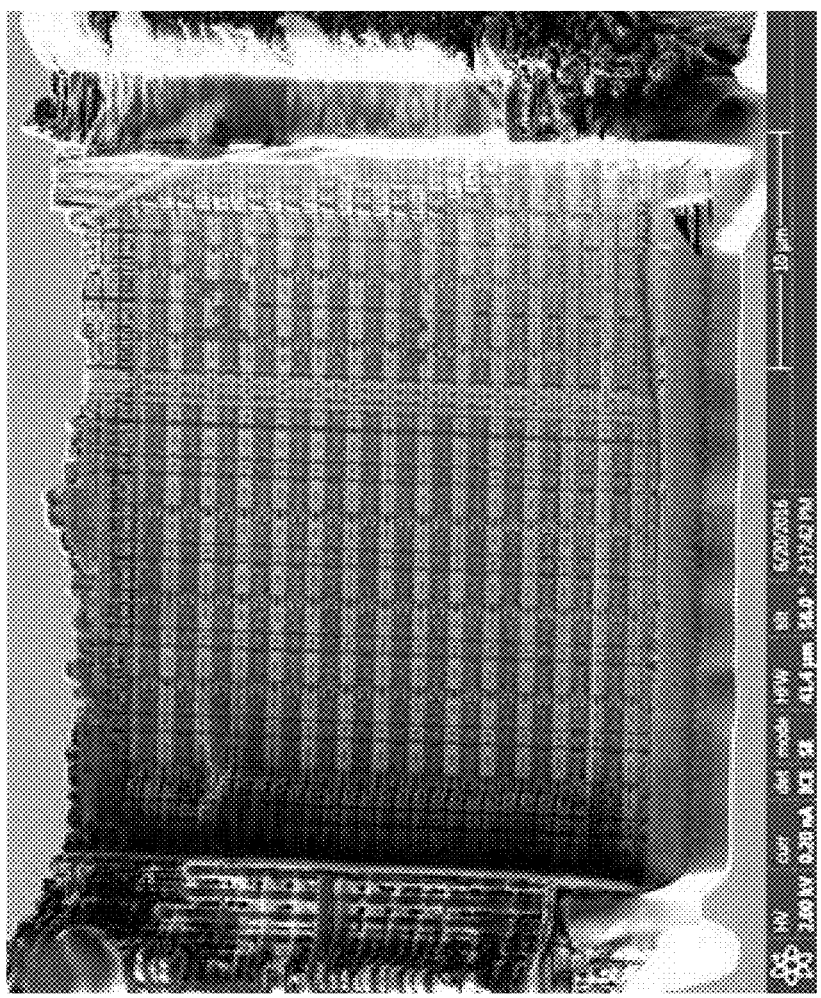
FIG. 2B is a SEM image of the nascent plan-view lamella of FIG. 2A after curtain artifacts on the surface of the exposed uppermost layer were removed over relatively large areas through PFIB-based, face-on, gas-assisted etching using MNA as a precursor gas.

FIG. 2B is a SEM image of the nascent plan-view lamella of FIG. 2A after curtain artifacts on the surface of the exposed uppermost layer were removed over relatively large areas through PFIB-based, face-on, gas-assisted etching using MNA as a precursor gas; over some areas, multiple metal layers were exposed. Both the removal of, and reduction in, curtain artifacts through PFIB-based, face-on, gas-assisted etching using MNA as a precursor gas evidences significant advantages for such etching in promoting planarity over large areas. Removal of curtain artifacts was accomplished using beam parameter ranges as described above for FIG. 1D.

Figure 2C:
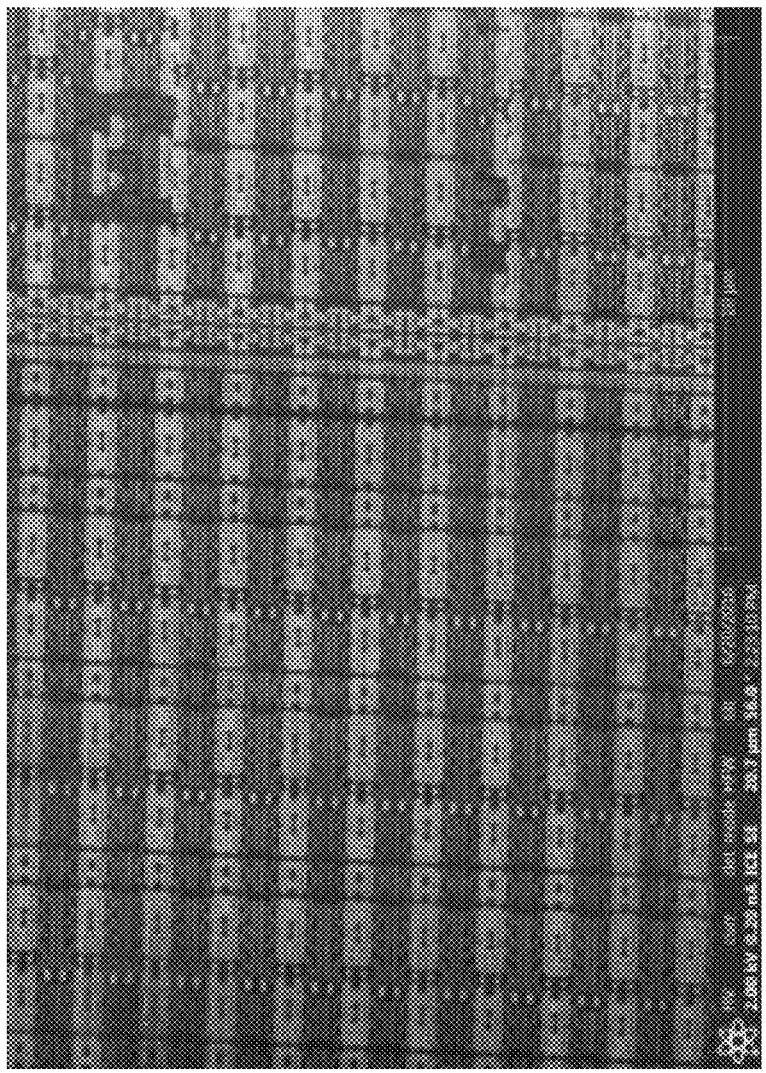
FIG. 2C is a higher magnification SEM image of a highly planar section (about 20 $\mu m \times 15$ $\mu m$=about 300 $\mu m^2$) from the lamella shown in FIG. 2A and FIG. 2B after thorough removal of curtain artifacts through PFIB-based, face-on, gas-assisted etching using MNA as a precursor gas.

FIG. 2C is a higher magnification SEM image of a section (about 20 μm×15 μm=about 300 μm2) from the nascent plan-view lamella shown in FIG. 2A and FIG. 2B after removal of curtain artifacts and planarization down to a single metal layer through PFIB-based, face-on, gas-assisted etching using MNA as a precursor gas. The SEM image demonstrates that curtain removal may be accomplished over a relatively large area using PFIB-based, face-on, gas-assisted etching using MNA as a precursor gas. In addition, the SEM image evidences the ability of PFIB-based, face-on, gas-assisted etching using MNA as a precursor gas to planarize a sample even when multiple metal layers are exposed. Again, removal of curtain artifacts and planarization was accomplished using beam parameter ranges as described above for FIG. 1D.

Figure 3A:
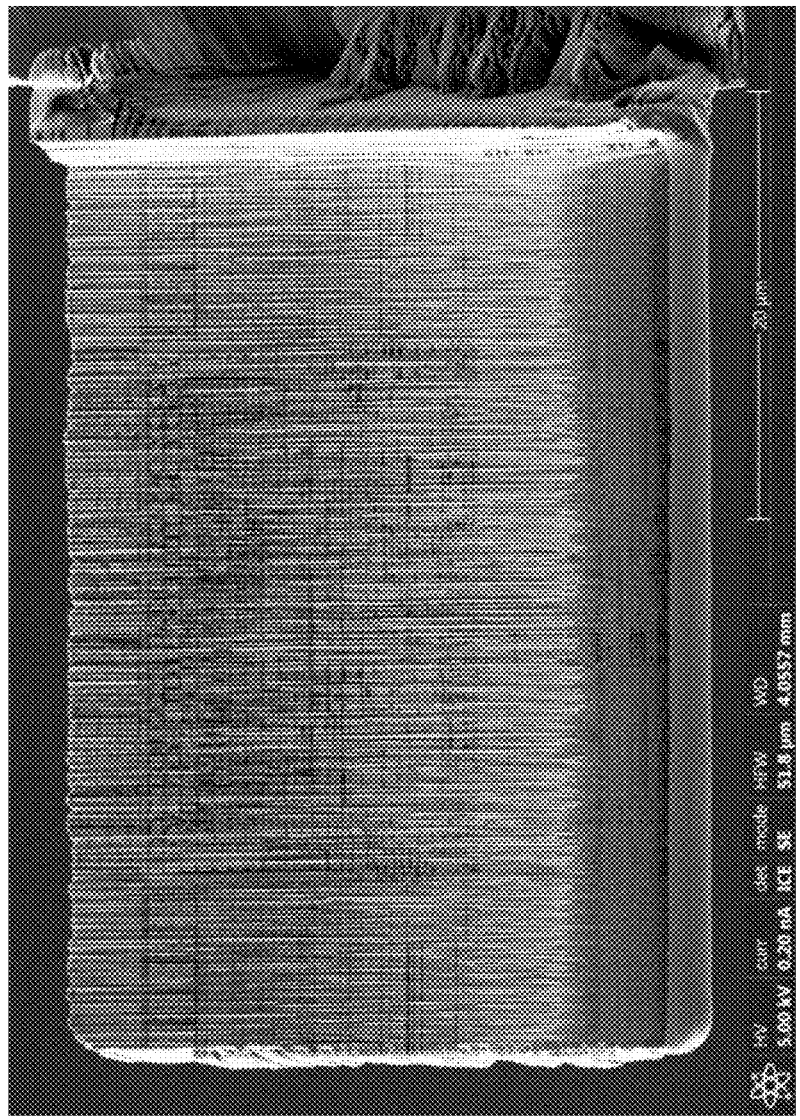
FIG. 3A is a SEM image of a face-view-prominent section of a lamella cut from a multilayered microelectronic device (the face area displayed appears to be about 40 $\mu m \times 25$ $\mu m$=about 1000 $\mu m^2$ but the face area is actually larger, e.g., about 40 $\mu m \times 40$ $\mu m$, because the upper edge of the face area is tilted away from the SEM objective lens so that the size of vertical features appears smaller than their actual size).

FIG. 3A is a SEM image of a face-view-prominent section of a sample cut from a multilayered microelectronic device (the face area displayed is larger than the apparent dimensions of about 40 μm×25 μm=about 1000 μm2 in view of the upper edge being tilted away from the SEM objective lens).

Figure 3B:
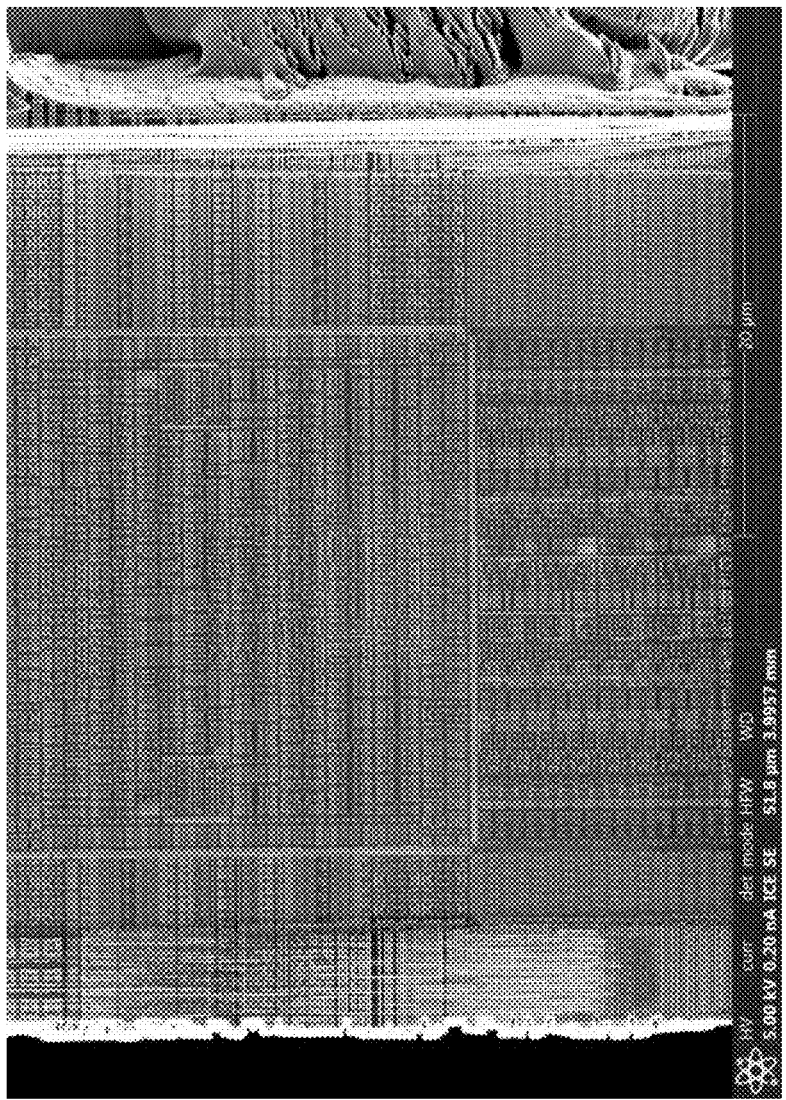
FIG. 3B is a SEM image of a section of a multilayered microelectronic device lamella like the one of FIG. 3A after a PFIB-based method of face-on, gas-assisted etching using MNA as a precursor gas was used for planarization and the removal of most curtain artifacts over a relatively large area (i.e., larger than about 20 $\mu m \times 20$ $\mu m$=about 400 $\mu m^2$).

FIG. 3B is a SEM image of a section of a multilayered microelectronic device sample like the one of FIG. 3A after a PFIB-based method of face-on, gas-assisted etching using MNA as a precursor gas was used to remove surface layer material, as well as most curtaining topography, over a large relatively area (for example, the relatively large square for which the upper edge of the image serves as a horizontal boundary is larger than about 20 μm×20 μm=about 400 μm2). In addition, this SEM image starkly evidences the capacity of the herein disclosed PFIB-based method for face-on, gas-assisted etching using MNA (or MNA-related chemical) gas as a precursor gas for thorough planarization of a surface even when multiple metal layers are exposed FIG. 4 contains two related STEM images of a 22 nm INTEL® SRAM address decoder. To obtain the left image (again, this left image corresponds to the image of FIG. 3B after: a 180° rotation; additional face-on, gas-assisted etching use MNA as a precursor gas; and additional backside thinning), a Helios G4FX™ dual beam system of FEI Company was used for STEM imaging (specifically, high-angle annular dark-field, or HAADF, imaging) of an area of about 35 μm×35 μm=about 1225 μm2 displaying uniform thickness (i.e., without curtaining or warping)—again, a quite expansive area, relatively. Achieving planarity over an area as large as the area in the field of view in the left image is far beyond the capabilities of conventional methods of preparing site-specific lamellae such as the previously-noted largely edge-on, Ga+ ion FIB-based methods.

Figure 4:
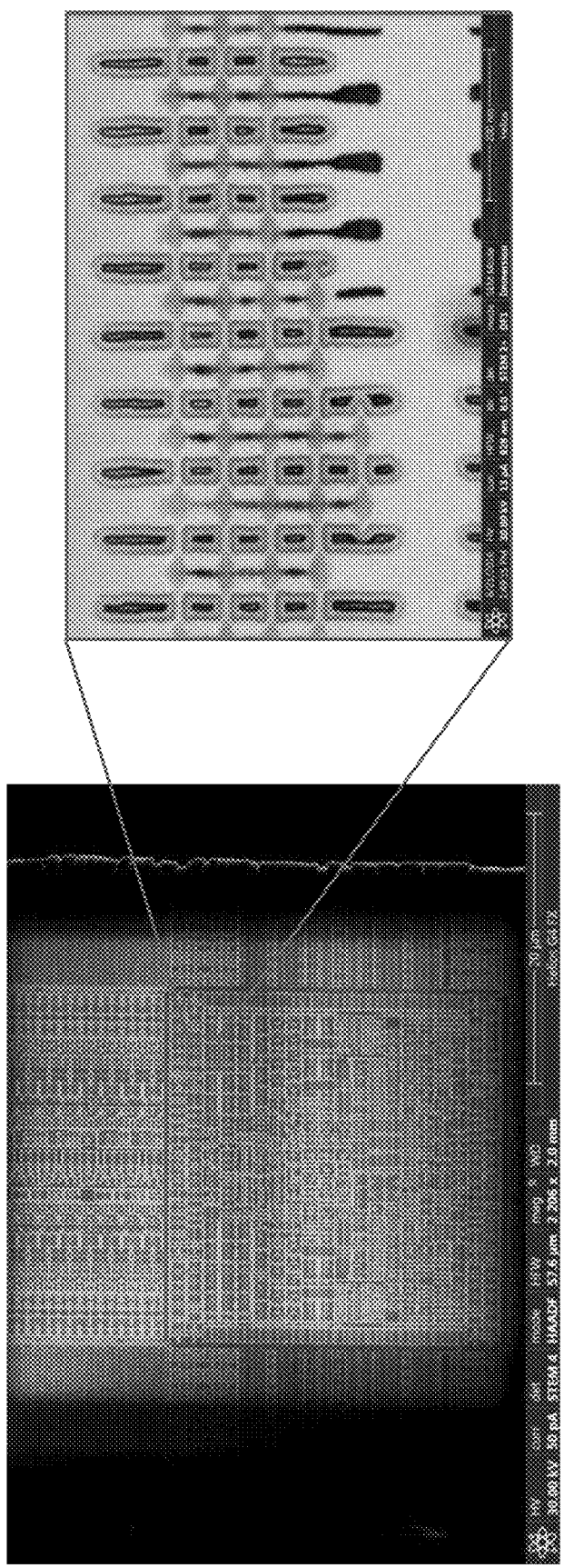
FIG. 4 contains two related images: the left image is a scanning TEM (STEM) image of a 22 nm INTEL® SRAM address decoder; a Helios G4FX™ dual beam system of Thermo Fisher Scientific Inc., was used for STEM imaging of an area of about 35 $\mu m \times 35$ $\mu m$=about 1225 $\mu m^2$ of uniform thickness (without curtaining or warping)—a relatively expansive area (this left image corresponds to the image of FIG. 3B after: a 180° rotation; additional face-on, gas-assisted etching using MNA as a precursor gas; and additional backside thinning); the right image is a STEM image of a much higher magnification of only a sub-section within the small rectangle overlayed on the left image (the displayed area in the right image being about 825 nm×550 nm=about 0.825 $\mu m \times 0.55$ $\mu m$=about 0.45 $\mu m^2$) of the 22 nm INTEL® SRAM address decoder.

The right image of FIG. 4 is also a STEM image, but one of only a small sub-section within the small rectangle overlayed on the left image of the 22 nm INTEL® SRAM address decoder, and at a much higher magnification. An approximate area of only about 0.45 μm2=about 825 nm×550 nm=about 0.825 μm×0.55 μm is displayed in the right image. To an even greater extent than the left image of FIG. 4, this right image impressively evidences how advantageously the herein disclosed FIB-based method of face-on, gas-assisted etching—using MNA (or MNA-related chemical) as a precursor gas—may be used to prepare a plan-view lamella having excellent electron transparency that is highly suited for sensitive STEM analysis.

Figure 5A:
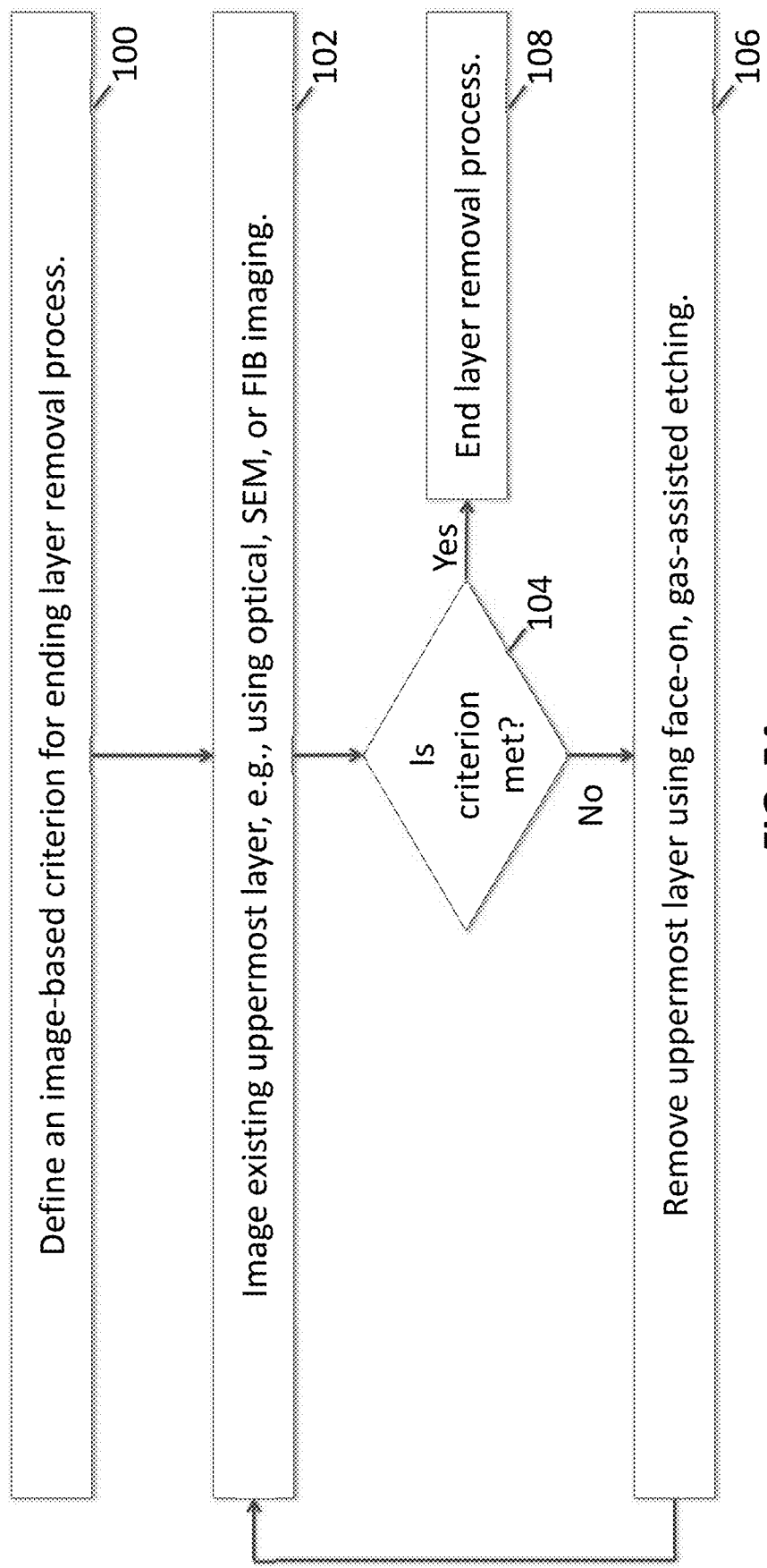
FIG. 5A and FIG. 5B are flow diagrams of implementations for automation of end-pointing in which face-on, gas-assisted etching is used in the successive removals of an uppermost layer, e.g., of a multilayered microelectronic device.

FIG. 5A is a flow diagram of an implementation for automation of end-pointing, i.e., ending a layer removal process at a specific layer, wherein face-on, gas-assisted etching is used in successive removals of an uppermost layer from a multilayered microelectronic device, and wherein whether an existing uppermost layer is removed is determined by whether that uppermost layer meets an image-based criterion.

At step 100, the process begins with entry of a defined image-based criterion for ending the layer removal process. Possible criteria may include, for example, the presence on an existing uppermost layer (as revealed through imaging) of a particular channel that connects a row of vias, or the presence on an existing uppermost layer of some distinctive planar-oriented circuit pattern. Either of these possible criteria or others may mark the existing uppermost layer as a layer comprising a region of interest (e.g., possibly a target area in the layer).

At step 102, the process continues with the imaging of the existing uppermost layer. The method of imaging the existing uppermost layer may be optical (e.g., based on the use of high resolution, high magnification optical microscopy) or, for example, based on the use of SEM imaging or FIB imaging. In view of the significant powers of magnification that may often be required, use of a method of charged particle beam microscopy, such as SEM or FIB imaging, may be used more frequently than an optical method, particularly when considering the convenience of using SEM imaging in conjunction with FIB milling in an applicable dual beam system such as a VION™ or a Helios NanoLab™ or a Scios™ or a Versa 3D DualBeam™ system—available from Thermo Fisher Company, ion block 104, the system determines whether, after data from the imaging of the uppermost layer is processed, the uppermost layer meets the entered image-based criterion. When the image-based criterion is met, the existing uppermost layer is left intact, and the process of successively removing an existing uppermost layer by FIB-based, face-on, gas-assisted etching using MNA (or MNA-related chemical) as a precursor gas, comes to an end at step 108. When the image-based criterion is not met, however, the process of successively removing an existing uppermost layer by FIB-based, face-on, gas-assisted etching using MNA (or MNA-related chemical) as a precursor gas continues with the removal of the current uppermost layer at step 106, after which the newly exposed uppermost layer is imaged at step 102, from which the process continues (as described above).

Figure 5B:
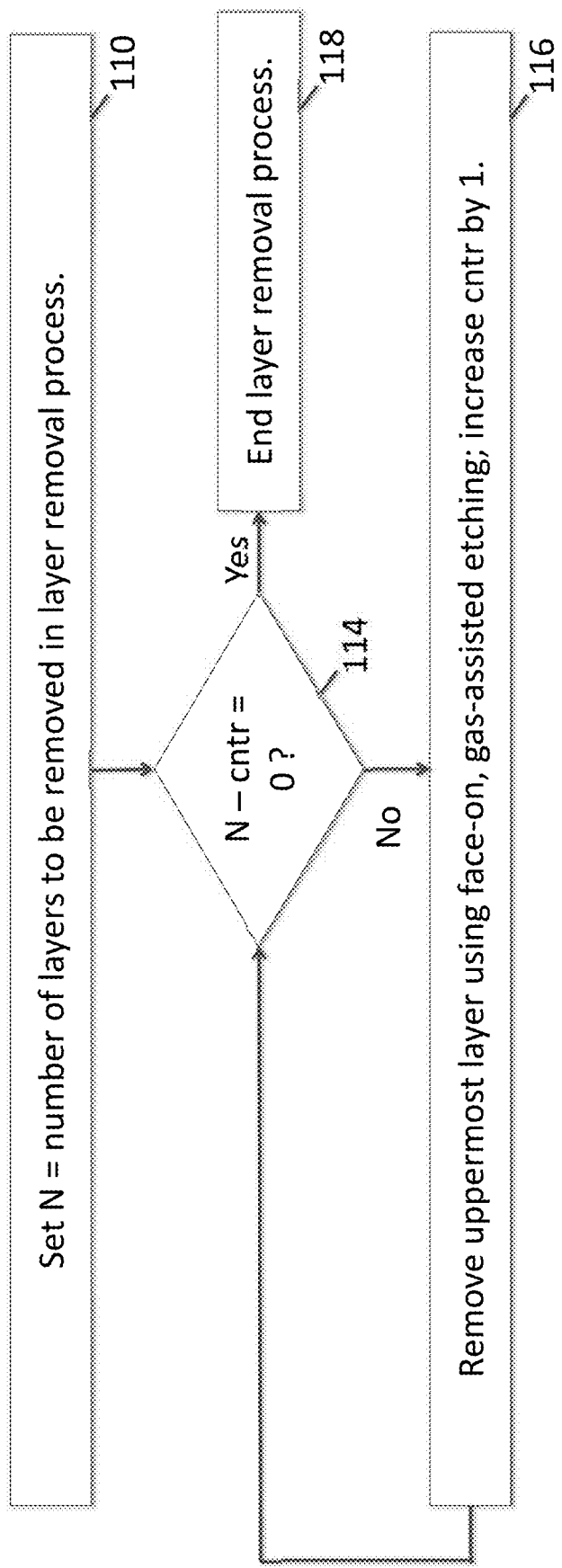

FIG. 5B is a flow diagram of a related embodiment or implementation for automation of end-pointing wherein a method of counting the number of layers removed is used in determining whether an existing uppermost layer is removed.

At step 110, the process begins with setting or entering an integer number (N) corresponding to a number of layers to be removed in the layer removal process. An operator may know, for example, that N layers cover a layer comprising a region of interest (e.g., possibly a target area in the layer). Accordingly, an operator would enter the integer value N for the number of layers to be removed.

At decision block 114, the system determines if N minus a counter of layers removed (cntr) equals zero. If N minus the counter of layers removed equals zero (i.e., "N−cntr=0 ?"), the layer removal process ends at step 118. If N minus the counter of layers removed does not equal zero, the process of successively removing an existing uppermost layer by FIB-based, face-on, gas-assisted etching using MNA (or MNA-related chemical) as a precursor gas continues at step 116 with the removal of the current uppermost layer, after which the counter of layers removed is increased by 1 (i.e., "increase cntr by 1") and the process continues again to decision block 114 (as described above in this paragraph).

In certain embodiments or implementations, a process for automation of end-pointing based on an image-based criterion may be combined with a process based on a method of counting. For example, a series of successive FIB-based, face-on, gas-assisted etchings {using MNA (or MNA-related chemical) as a precursor gas} of the multilayered microelectronic device possibly may already have resulted in the removal of, for example, at least 15 layers of the device. Accordingly, an existing uppermost layer would then be known to represent a layer that would be found below at least 15 layers in the original multilayered microelectronic device. The actual specific layer that the existing uppermost layer represents could then be conclusively identified through image-based evidence, e.g., through a finding that an image for a planar-oriented circuit pattern (complete or partial) from that existing uppermost layer corresponds to a known planar-oriented circuit pattern of a specific layer that is also found below at least 15 layers in the original multilayered microelectronic device. In additional embodiments or implementations, one or more other endpoint criteria may be utilized (i.e., beyond an image-based criterion or the simple above-outlined counting methodologies). For example, a real-time measurement of "stage current" or a secondary electron (SE) signal (or both) as determined by a SE detector during FIB milling may be displayed as scrolling, live-updated plots on a monitor graph. Levels of such stage current or SE signal data may rise and fall as layers of the multilayered microelectronics device are exposed and removed. That is, these levels may provide endpoint signals, e.g., in that counting peaks or other undulations in such levels may also be used to track the removal of layers in z space.

Figure 6:
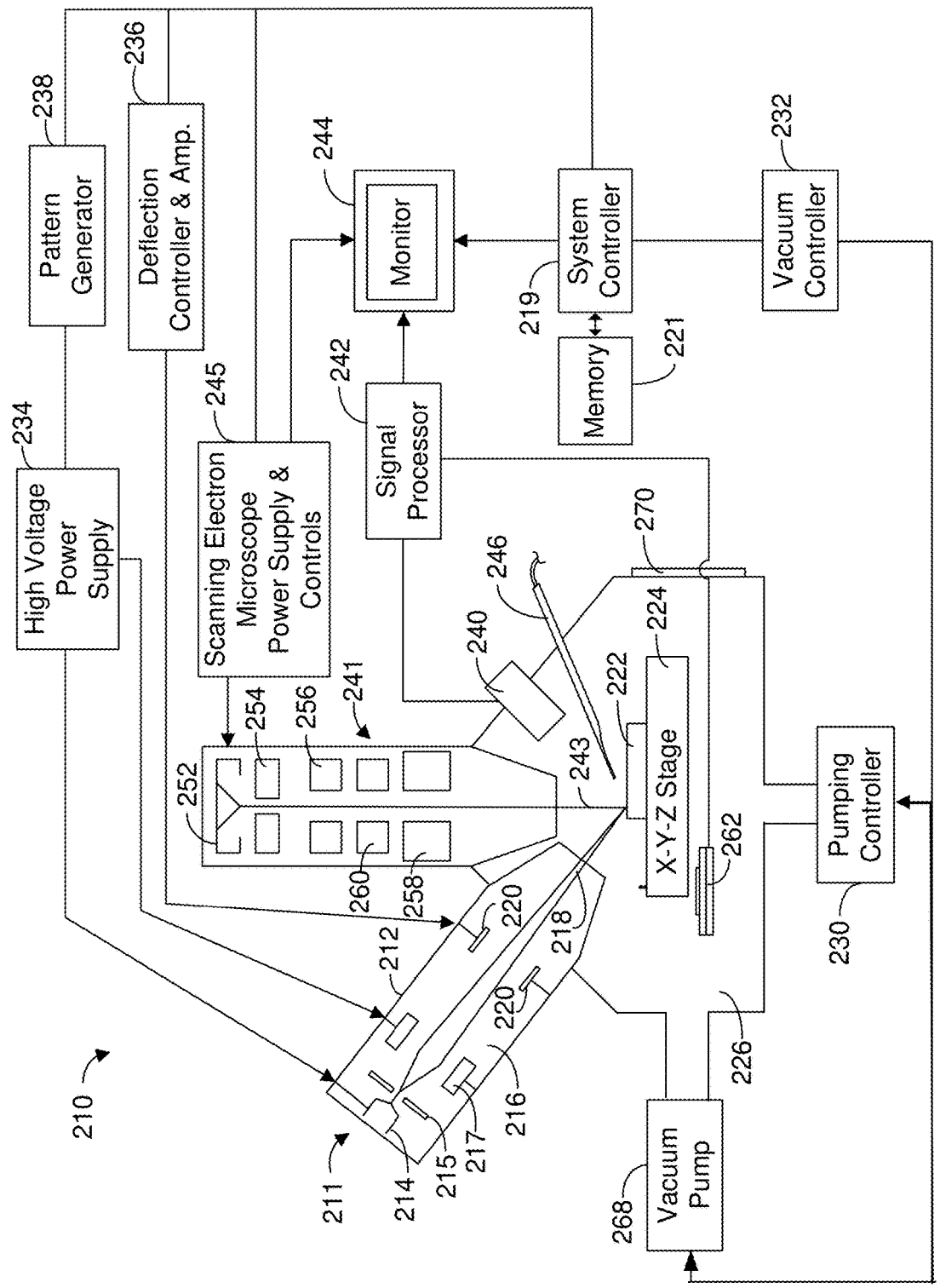
FIG. 6 illustrates a typical dual beam FIB/SEM system that could be used to implement aspects of the present invention.

FIG. 6 shows a typical dual beam FIB/SEM system 210 that could be used in implementations of aspects of the present invention. One implementation utilizes a dual beam FIB/SEM system 210 that uses an ion beam that is either normal or tilted by a few degrees to the plane of the sample surface and an electron beam having an axis that is also tilted, e.g., 52 degrees from the axis of ion beam. In some implementations, the ion beam and electron beam are capable of aligning so that the fields of view of both beams are coincident to within a few microns or less. The ion beam is typically used to image and machine the work piece, and the electron beam is used primarily for imaging but can also be used for some modification of the work piece. The electron beam will typically produce an image of a higher resolution than the ion beam image, and it will not damage the viewed surface like the ion beam. The image formed by the two beams can look different, and the two beams can therefore provide more information than a single beam.

Such a dual beam system could be made from discrete components or alternatively, could be derived from a conventional device such as, again, a VION™ or a Helios NanoLab™ or a Scios™ or a Versa 3D DualBeam™ system—available from Thermo Fisher Scientific Inc. Implementations using other particle beam systems, including for example, single beam systems, such as FIB- or SEM-only systems, or dual beam systems having two FIB columns, may also be useful.

Focused ion beam system 210 includes an evacuated envelope 211 having an upper neck portion 212 within which are located an ion source 214 and a focusing column 216 including extractor electrodes 215 and an electrostatic optical system 217. Ion beam 218 passes from ion source 214 through column 216 and between electrostatic deflection means schematically indicated at 220 toward work piece 222, which comprises, for example, a semiconductor device positioned on movable X-Y-Z stage 224 within lower chamber 226. An ion pump or other pumping system (not shown) can be employed to evacuate neck portion 212. The chamber 226 is evacuated with turbomolecular and mechanical pumping system 268 under the control of pumping controller 230. The vacuum system provides within chamber 226 a vacuum of between, e.g., approximately $5 \times 10^{-8}$ Torr and $5 \times 10^{-4}$ Torr. If an etch-assisting, an etch retarding, or a deposition precursor gas is used, the chamber background pressure may rise, e.g., to about $1 \times 10^{-5}$ Torr.

High voltage power supply 234 is connected to ion source 214 as well as to appropriate electrodes in focusing column 216 for forming an ion beam 218 and directing the same downwardly. Deflection controller and amplifier 236, operated in accordance with a prescribed pattern provided by pattern generator 238, is coupled to deflection plates 220 whereby beam 218 may be controlled to trace out a corresponding pattern on the upper surface of work piece 222. In some systems the deflection plates are placed before the final lens, as is well known in the art.

The ion source 214 typically provides a metal ion beam of gallium, although other ion sources, such as a multicusp or other plasma ion source, can be used. The ion source 214 typically is capable of being focused into a sub one-tenth micron wide beam at work piece 222 for either modifying the work piece 222 by ion milling, enhanced etch, material deposition, or for the purpose of imaging the work piece 222. A charged particle multiplier 240 used for detecting secondary ion—or, e.g., as a secondary electron detector 240 for detecting secondary electron—emission for imaging is connected to signal processor 242, where the signals from charged particle multiplier 240 are amplified, converted into digital signals, and subjected to signal processing. The resulting digital signal is to display an image of work piece 222 on the monitor 244.

A scanning electron microscope 241, along with power supply and control unit 245, is also provided with the FIB/SEM system 210. An electron beam 243 is emitted from a cathode 252 by applying voltage between cathode 252 and an anode 254. Electron beam 243 is focused to a fine spot by means of a condensing lens 256 and an objective lens 258. Electron beam 243 is scanned two-dimensionally on the specimen by means of a deflection coil 260. Operation of condensing lens 256, objective lens 258, and deflection coil 260 is controlled by power supply and control unit 245.

Electron beam 243 can be focused onto work piece 222, which is on movable X-Y-Z stage 224 within lower chamber 226. Scanning electron microscope 241 produces a finely focused electron beam 243, which is scanned across the surface of the structure, preferably in a raster pattern. When the electrons in the electron beam 243 strike the surface of work piece 222, secondary electrons and backscattered electrons are emitted. Respectively, these electrons are detected by SE detector 240 or backscattered electron detector 262. The analog signal produced either by SE detector 240 or backscattered electron detector 262 is amplified and converted into a digital brightness value by signal processor unit 242. The resulting digital signal can be displayed as an image of work piece 222 on the monitor 244.

A door 270 is opened for inserting work piece 222 onto stage 224, which may be heated or cooled, and also for servicing an internal gas supply reservoir, if one is used. The door is interlocked so that it cannot be opened if the system is under vacuum. The high voltage power supply provides an appropriate acceleration voltage to electrodes in ion beam column 216 for energizing and focusing ion beam 218.

A gas delivery system 246 extends into lower chamber 226 for introducing and directing a gaseous vapor toward work piece 222. A gas delivery system 246 is described in (8) U.S. Pat. No. 5,851,413 (the '413 patent—issued Dec. 12, 1998) to Casella et al., "Gas delivery systems for particle beam processing," which is herein incorporated by reference in its entirety. Another gas delivery system is described in (9) U.S. Pat. No. 5,435,850 (the '850 patent—issued Jul. 25, 1995) to Rasmussen, "Gas Injection System," which is also herein incorporated by reference in its entirety. For example, Dx (or MNA-related chemical) gas can be delivered to enhance curtain removal or planarization of a lamella surface from a microelectronic device, or a metal organic compound can be delivered to deposit a metal.

System controller 219 controls the operations of the various parts of dual beam system 210. Through system controller 219, a user can cause ion beam 218 or electron beam 243 to be scanned in a desired manner through commands entered into a conventional user interface (not shown). System controller 219 can also comprise computer-readable memory 221 and may control dual beam system 210 in accordance with data or programmed instructions stored in memory 221, such as programmed instructions for automation of end-pointing. Computer aided design (CAD) data concerning the sample/semiconductor stored in memory 221 can be used to create a CAD polygon overlay or other positional data used to locate a feature of interest and alignment points or transfer fiducials as described above.

Apparatuses and systems described above may utilize high-accuracy beam placement method for local area navigation. Further, it should be recognized that elements, aspects or embodiments can be implemented via computer hardware or software, or a combination of both. Methods can be implemented in computer programs using standard programming techniques-including a computer-readable storage medium configured with a computer program, where the storage medium so configured causes a computer to operate in a specific and predefined manner-according to the methods and figures described in this specification. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits programmed for that purpose.

Further, methodologies may be implemented in any type of computing platform, including but not limited to, personal computers, mini-computers, main-frames, workstations, networked or distributed computing environments, computer platforms separate, integral to, or in communication with charged particle tools or other imaging devices, and the like. Aspects may be implemented in machine readable code stored on a storage medium or device, whether removable or integral to the computing platform, such as a hard disc, optical read and/or write storage mediums, RAM, ROM, and the like, so that it is readable by a programmable computer, for configuring and operating the computer when the storage media or device is read by the computer to perform the procedures described herein. Moreover, machine readable code, or portions thereof, may be transmitted over a wired or wireless network. Implementations described herein may include these and other various types of computer-readable storage media when such media contain instructions or programs for implementing the steps described above in conjunction with a microprocessor or other data processor. Implementations may also include the computer itself when programmed according to the methods and techniques described herein.

Computer programs can be applied to input data to perform the functions described herein and thereby transform the input data to generate output data. The output information is applied to one or more output devices such as a display monitor. In some implementations, the transformed data may represent physical and tangible objects, including producing a particular visual depiction of the physical and tangible objects on a display.

As indicated, some implementations may also make use of a particle beam apparatus, such as a FIB or SEM, in order to image a sample using a beam of particles. Such particles used to image a sample may inherently interact with the sample resulting in some degree of physical transformation. Further, throughout the present specification, discussions utilizing terms such as "calculating," "determining," "measuring," "generating," "detecting," "forming," or the like, also refer to the action and processes of a computer system, or similar electronic device, that manipulates and transforms data represented as physical quantities within the computer system into other data similarly represented as physical quantities within the computer system or other information storage, transmission or display devices.

Particle beam systems suitable for carrying out implementations are commercially available, for example, from Thermo Fisher Scientific. However, even though much of the previous description is directed toward the use of FIB or plasma FIB (PFIB) etching, milling, and deposition, the beam used to image or process the desired samples could comprise, for example, an electron beam, a laser beam, or some other shaped ion beam, for example, from a liquid metal ion source, or another charged particle beam source. Further, although much of the previous description is directed at particle beam systems, implementations could be applied to any suitable sample control system employing a moveable sample stage to navigate to the location of a sample feature.

Although much of the previous description has application to modifying semiconductor wafers, implementations could be applied to any suitable substrate or surface. Further, whenever the terms "automatic," "automated," or similar terms are used herein, those terms will be understood to include manual initiation of the automatic or automated process or step. In the following discussion and in the claims, the terms "including" and "comprising" are used in an open-ended fashion, and thus should be interpreted to mean "including, but not limited to . . . " The term "integrated circuit" refers to a set of electronic components and their interconnections (internal electrical circuit elements, collectively) that are patterned on the surface of a microchip. The term "semiconductor device" refers generically to an integrated circuit (IC), which may be integral to a semiconductor wafer, separated from a wafer, or packaged for use on a circuit board. The term "FIB" or "focused ion beam" is used herein to refer to any collimated ion beam, including a beam focused by ion optics and shaped ion beams.

To the extent that any term is not specially defined in this specification, the intent is that the term is to be given its plain and ordinary meaning. The accompanying drawings are intended to aid in understanding the present invention and, unless otherwise indicated, are not drawn to scale.

The invention has broad applicability and can provide many benefits as described and shown in the examples above. Embodiments or implementations will vary depending upon the specific application, and not every embodiment or implementation will provide all of the benefits and meet all of the objectives that are achievable by the invention.

Although the present invention and its advantages have been described in detail, it should be understood that various changes, substitutions and alterations can be made to the embodiments or implementations described herein without departing from the spirit and scope of the invention as defined by the appended claims. Moreover, the scope of the present application is not intended to be limited to the particular embodiments or implementations of the process, machine, manufacture, composition of matter, means, methods and steps described in the specification. As one of ordinary skill in the art will readily appreciate from the disclosure processes, machines, manufacture, compositions of matter, means, methods, or steps, presently existing or later to be developed that perform substantially the same function or achieve substantially the same result as the corresponding embodiments or implementations described herein may be utilized according to the present invention. Accordingly, the appended claims are intended to include within their scope such processes, machines, manufacture, compositions of matter, means, methods, or steps.

REFERENCES (1) R. Anderson and S. J. Klepies, Practical aspects of FIB specimen preparation, with emphasis on semiconductor applications, In: L. A. Giannuzzi & F. A. Stevie (ed's) Introduction to Focused Ion Beams—Instrumentation, Theory, Techniques and Practice. Springer Science, pp. 173-200 (2005).

(2) L. A. Giannuzzi, B. W. Kempshall, S. M. Schwarz, J. K. Lomness, B. I. Prenitzer, and F. A. Stevie, FIB lift-out specimen preparation techniques: ex-situ and in-situ methods, In: L. A. Giannuzzi & F. A. Stevie (ed's) Introduction to Focused Ion Beams—Instrumentation, Theory, Techniques and Practice. Springer Science, pp. 201-228 (2005).

(3) U.S. Pat. No. 7,423,263 (the '263 patent—issued Sep. 9, 2008) to Liang Hong, Craig Henry, Jay Jordan, and Young-Chung Wang, "Planar view sample preparation" (Assignee: FEI Company).

(4) J. Mayer, L. A. Giannuzzi, T. Kmino, and J. Michael, TEM Sample Preparation and FIB-Induced Damage, MRS [Materials Research Society] Bulletin, Vol. 32, pp. 400-407 (May 2007).

(5) U.S. Pat. Appl. Pub. No. 20160126060 (the '060 patent application—published May 5, 2016) to Scott Edward Fuller, Jason Donald, and Termsupt Seemuntchaibowarn, "Endpointing for focused ion beam processing" (Applicant for parent PCT: FEI Company).

(6) U.S. Pat. Appl. Pub. No. 20130328246 (the '246 patent application—published Dec. 12, 2013) to Andrew B. Wells, William Parker, Clive D. Chandler, and Mark W. Utlaut, "Lamella creation method and device using fixed-angle beam and rotating sample stage" (Assignee: FEI Company).

(7) U.S. Pat. No. 9,064,811 (the '811 patent—issued Jun. 23, 2015) to Chad Rue and Clive D. Chandler, Precursor for planar deprocessing of semiconductor devices using a focused ion beam" (Assignee: FEI Company).

(8) U.S. Pat. No. 5,851,413 (the '413 patent—issued Dec. 12, 1998) to Robert A. Casella, Charles J. Libby, and Gary P. Rathmell, "Gas delivery systems for particle beam processing" (Assignee: Micrion Corporation).

(9) U.S. Pat. No. 5,435,850 (the '850 patent—issued Jul. 25, 1995) to Jorgen Rasmussen, "Gas Injection System" (Assignee: FEI Company).

We claim as follows:

1. A method of fabricating, from a sample extracted from a semiconductor work piece, a lamella including an electron-transparent portion including a region of interest, the semiconductor work piece having multiple layers parallel to its surface, the method comprising:

directing a focused ion beam toward the work piece to cut the sample from the work piece;

directing a focused ion beam oriented parallel to multiple layers toward the sample to thin the sample to form the lamella;

providing an etch-assisting gas at the surface of the lamella, the etch gas including methyl nitroacetate, methyl acetate, ethyl acetate, ethyl nitroacetate, propyl acetate, propyl nitroacetate, nitro ethyl acetate, methyl methoxyacetate, methoxy acetylchloride, or combinations thereof; and directing a focused ion beam oriented perpendicularly to the multiple layers toward the lamella to thin in the presence of the etch-assisting gas a portion of the lamella to produce the electron-transparent portion including the region of interest.

2. The method of claim 1 in which directing a focused ion beam oriented perpendicularly to the multiple layers toward the lamella to thin in the presence of the etch-assisting gas a portion of the lamella comprises milling the portion of the lamella to produce an electron transparent region having a thickness of less than 100 nm, the electron transparent region essentially surrounded by a frame having a thickness at least 100 nm thicker than the thickness of the electron transparent region.

3. The method of claim 1 in which directing a focused ion beam oriented perpendicularly to the multiple layers toward the lamella to thin in the presence of the etch-assisting gas a portion of the lamella comprises planarizing the surface of the portion of lamella to remove curtaining and other artifacts.

4. The method of claim 1, further comprising:
performing multiple repetitions of the steps of:
providing the etch-assisting gas at the surface of the lamella; and
directing a focused ion beam oriented perpendicularly to the multiple layers toward the lamella to thin in the presence of the etch-assisting gas a portion of the lamella;
forming an ion beam image of the lamella after at least one of the repetitions; and
determining from the ion beam image when to cease the repetitions.

5. The method of claim 4 in which determining from the ion beam image when to cease the repetitions comprises determining to cease the repetitions when the region of interest is visible in the ion beam image.

6. A plan-view lamella prepared by the method of claim 1.

7. The lamella of claim 6 in which:
the electron transparent region has an area of greater than 50 $\mu m^2$;
the electron transparent region has a thickness of less than 100 nm;
the electron transparent region is essentially surrounded by a frame having a thickness at least 100 nm thicker than the thickness of the electron transparent region.

8. The lamella of claim 6 in which the electron transparent portion has an area larger than about 50 $\mu m^2$.

9. The lamella of claim 6 in which the electron transparent portion has thickness less than about 50 nm.

10. A method of preparing a plan-view lamella from a multilayered microelectronic device, the method comprising:
(a) directing a focused ion beam towards a work piece to separate a sample from a work piece, the sample having a target area parallel to the surface of the work piece;
(b) bulk thinning the sample by directing the focused ion beam toward the sample approximately parallel to the target area to remove material above the target area;
(c) final thinning the sample to form a lamella including the target area by:
(c1) directing an etch-assisting gas toward an uppermost layer over the target area, the etch-assisting gas including one or more compounds selected from a group consisting essentially of methyl nitroacetate, methyl acetate, ethyl acetate, ethyl nitroacetate, propyl acetate, propyl nitroacetate, nitro ethyl acetate, methyl methoxyacetate, and methoxy acetylchloride;
(c2) directing a focused ion beam in a face-on orientation toward the uppermost layer over the target area, thereby removing the uppermost layer and exposing an underlying layer over, or comprising, the target area; and
repeating steps (c1) and (c2) until the exposed underlying layer is the one comprising the target area.

11. The method of claim 10 in which the focused ion beam originates from a plasma focused ion beam source.

12. The method of claim 10 in which directing a focused ion beam in a face-on orientation toward the uppermost layer over the target area comprises directing a focused ion beam in which the ions have landing energies of less than about 12 keV.

13. The method of claim 10 in which step (c) forms a square area having an electron transparency suitable for TEM analyses within the target area both is larger than at least about 5 $\mu m$ by 5 $\mu m$ and is within an overall area of electron transparency suitable for such TEM analyses that is larger than at least about 100 $\mu m^2$.

14. The method of claim 13 in which the sample thickness within the square area is less than about 100 nm.

15. The method of claim 10 further comprising removing a backside layer underlying the target area by:
re-orienting the device so that the focused ion beam is directed face-on to the device's backside and, after the re-orienting, the backside layer is over the target area;
directing an etch-assisting gas toward the backside layer;
directing a focused ion beam toward the backside layer, thereby removing a backside layer;
in which:
the etch-assisting gas comprises one or more compounds selected from a group consisting of xenon difluoride, DE, methyl nitroacetate, methyl acetate, ethyl acetate, ethyl nitroacetate, propyl acetate, propyl nitroacetate, nitro ethyl acetate, methyl methoxyacetate, and methoxy acetylchloride; and
the focused ion beam mills away the exposed backside layer in a face-on orientation.

16. The method of claim 10 in which repeating steps (c1) and (c2) until the exposed underlying layer is the one comprising the target area further comprises determining when the exposed underlying layer is the one comprising the target area by:
acquiring an image of the exposed underlying layer; and
automatically evaluating the exposed underlying layer to determine whether the exposed underlying layer is one comprising the target area.

17. A method of claim 10 in which repeating steps (c1) and (c2) until the exposed underlying layer is the one comprising the target area further comprises determining when the exposed underlying layer is the one comprising the target area by:
acquiring an image an exposed underlying layer;
determining a number of additional layers to be removed to expose the target area; and
as additional layers are removed, counting the number of layers removed until the determined number of additional layers has been removed, leaving the target area exposed.

18. A method of curtain artifact removal from a target area of an exposed layer, the method comprising:
(a) defining a target area containing a curtain artifact on an exposed layer;
(b) directing an etch-assisting gas toward the target area; and
(c) directing a focused ion beam toward the target area, thereby removing the curtain artifact from the target area;
in which:
the etch-assisting gas comprises at least one chemical or more selected from a group consisting of methyl nitroacetate, methyl acetate, ethyl acetate, ethyl nitroacetate, propyl acetate, propyl nitroacetate, nitro ethyl acetate, methyl methoxyacetate, and methoxy acetylchloride; and the focused ion beam mills away the curtain artifact in a face-on orientation.

19. The method of claim 18 in which the focused ion beam operates during curtain artifact removal at an acceleration voltage ranging from about 5 keV to about 12 keV.

* * * * *